United States Patent
Yerramilli et al.

(10) Patent No.: US 10,725,052 B2
(45) Date of Patent: Jul. 28, 2020

(54) METHODS AND COMPOSITIONS FOR THE DETECTION AND DIAGNOSIS OF RENAL DISEASE AND PERIODONTAL DISEASE

(71) Applicant: IDEXX Laboratories, Inc., Westbrook, ME (US)

(72) Inventors: Mahalakshmi Yerramilli, Falmouth, ME (US); Giosi Farace, Georgetown, ME (US); John J. Quinn, Falmouth, ME (US); Murthy V. S. N. Yerramilli, Falmouth, ME (US)

(73) Assignee: IDEXX LABORATORIES, INC., Westbrook, ME (US)

( * ) Notice: Subject to any disclaimer, the term of this patent is extended or adjusted under 35 U.S.C. 154(b) by 361 days.

(21) Appl. No.: 15/447,789

(22) Filed: Mar. 2, 2017

(65) Prior Publication Data

US 2017/0269101 A1  Sep. 21, 2017

Related U.S. Application Data

(60) Provisional application No. 62/302,299, filed on Mar. 2, 2016.

(51) Int. Cl.
*G01N 33/68* (2006.01)
*C07K 14/81* (2006.01)
*C07K 16/38* (2006.01)

(52) U.S. Cl.
CPC ..... *G01N 33/6893* (2013.01); *C07K 14/8139* (2013.01); *C07K 16/38* (2013.01); *G01N 2333/8139* (2013.01); *G01N 2800/18* (2013.01); *G01N 2800/347* (2013.01); *G01N 2800/348* (2013.01); *G01N 2800/52* (2013.01)

(58) Field of Classification Search
CPC ....... G01N 33/6893; G01N 2333/8139; G01N 2800/18; G01N 2800/347; G01N 2800/348; G01N 2800/52; C07K 14/8139; C07K 16/38
See application file for complete search history.

(56) References Cited

U.S. PATENT DOCUMENTS

| | | |
|---|---|---|
| 5,726,010 A | 3/1998 | Clark |
| 2007/0087448 A1 | 4/2007 | Nelsestuen |
| 2007/0105114 A1 | 5/2007 | Li |
| 2007/0212738 A1 | 9/2007 | Haley |
| 2008/0064047 A1 | 3/2008 | Letter |
| 2009/0023165 A1 | 1/2009 | Haigh |
| 2010/0145398 A1 | 6/2010 | Li |
| 2013/0130285 A1* | 5/2013 | Atkinson ........... G01N 33/5308 435/7.92 |

FOREIGN PATENT DOCUMENTS

| | | |
|---|---|---|
| WO | 04/002518 A1 | 1/2004 |
| WO | 04/048598 A2 | 6/2004 |
| WO | 06/081473 A2 | 8/2006 |
| WO | 07/013575 A2 | 2/2007 |
| WO | 08/021290 A2 | 2/2008 |
| WO | 10/057184 A2 | 5/2010 |
| WO | 11/079280 A2 | 6/2011 |
| WO | 11/153469 A1 | 12/2011 |

OTHER PUBLICATIONS

GenBank Acc: DN333728.1 (LIB3184-050-P2-K1-G3 LIB3184 Canis lupus familiaris cDNA clone CLN1567511, mRNA sequence), Mar. 4, 2005.
GenBank Acc: DN433099.1 (LIB4217-072-R1-K1-B5 LIB4217 Canis lupus familiaris cDNA clone CLN10822937, mRNA sequence), Mar. 8, 2005.
GenBank Acc: DN378132.1 (LIB38533_037_E02_T7_1 LIB38533 Canis lupus familiaris cDNA clone LIB38533_37_E02, mRNA sequence), Mar. 7, 2005.
GenBank Acc: DN379768.1 (LIB38533_018_G01_T7_1 LIB38533 Canis lupus familiaris cDNA clone LIB38533_18_G01, mRNA sequence), Mar. 7, 2005.
GenBank: DR105799.1 (JHU098B10L680 Canine cardiovascular system biased cDNA Canis lupus familiaris cDNA similar to Hs cystatin B (stefin B) (CSTB), mRNA sequence), Jun. 13, 2005.
GenBank: DN372492.1 (LIB3733046A1K1F12 LIB3733 Canis lupus familiaris cDNA clone CLN12921389, mRNA sequence), Mar. 7, 2005.
UniProtKB P04080 (CYTB_HUMAN) >sp|P04080|CYTB_HUMAN Cystatin-B OS=*Homo sapiens* OX=9606 GN=CSTB PE=1 SV=2 MMCGAPSATQPATAETQHIADQVRSQLEEKENKKFPV FKAVSFKSQVVAGTNYFIKVHVG DEDFVHLRVFQSLPHENKPLTLSNYQTNKAKHDELTYF, Feb. 13, 2019.
UniProtKB P01041 (CYTB_RAT) >sp|P01041|CYTB_RAT Cystatin-B OS=Rattus norvegicus OX=10116 GN=Cstb PE=1 Sv=1 MMCGA PSATMPATTETQEIADKVKSQLEEKANQKFDVFKAISFRRQV VAGTNFFIKVDVG EEKCVHLRVFEPLPHENKPLTLSSYQTDKEKHDELTYF, Jan. 16, 2019
UniProtKB P25417 (CYTB_BOVIN) >sp|P25417|CYTB_BOVIN Cystatin-B OS=Bos taurus OX=9913 GN=CSTB PE=1 SV=1 MMCGG TSATQPATAETQAIADKVKSQLEEKENKKFPVFKALEFKSQL VAGKNYFIKVQVD EDDFVHIRVFESLPHENKPVALTSYQTNKGRHDELTYF, Jan. 16, 2019.
UniProtKB Q29290 (CYTB_PIG) >sp|Q29290|1CYTB_PIG Cystatin-B OS=Sus scrofa OX=9823 GN=CSTB PE=1 SV=1 MMCGA PSATQPATAEIQAIADKVKSQLEEKENKTFPVFKAVEFKSQVV AGRNLFIKVQVD DDDFVHLRVFESLPHENKPLTLSSYQTNKSRHDELTYF, Dec. 5, 2018

(Continued)

*Primary Examiner* — Andrea S Grossman
(74) *Attorney, Agent, or Firm* — DLA Piper LLP

(57) ABSTRACT

The disclosure provides compositions and methods for the detection of renal disease and periodontal disease in mammals.

12 Claims, 10 Drawing Sheets

Specification includes a Sequence Listing.

(56) References Cited

OTHER PUBLICATIONS

UniProtKB Q10994 (CYTB_SHEEP) >sp|Q10994|CYTB_SHEEP Cystatin-B OS=Ovis aries OX=9940 GN=CSTB PE=1 SV=1 MMCGAPSATQPATAETQAIADKVKSQLEEKENKKFPVFKALEFKSQLVAGKNYFIKVQVDEDDFVHIRVFESLPHENKPVALTSYQTNKGRHDELTYF, Apr. 10, 2019
UniProtKB F1PS73 (F1PS73_CANLF) >tr|F1PS73|F1PS73_CANLF Cystatin B OS=Canis lupus familiaris OX=9615 GN=CSTB PE=4 SV=2 QVKAQLEERENKKYTTFKAVTFRSQVVAGTPYFIKVQVDDDEFVHLRVFQSLPHENKPLALSSYQTNKAKHDELAYF, May 3, 2011.
Joronen et al., "Detection of low molecular weight cysteine proteinase inhibitors by time-resolved fluoroimmunoassay", Journal of Immunological Methods, 86(2):243-247 (1986).
Lee et al., "Identification of cystatin B as a potential serum marker in hepatocellular carcinoma", Clinical Cancer Research, 14(4):1080-1089 (2008).
Ji et al., "Development of a fluorescent microsphere immunoassay for cystatin B (CSTB) in serum of patients with hepatocellular carcinoma", Clinical Chemistry and Laboratory Medicine, 49(1):151-155 (2011).
Kopitar-Jerala et al., "Monoclonal antibodies to human stefin B and determination of their epitopes", Biochimica et Biophysica Acta. Protein Structure and Molecular Enzymology, 1164(1):75-80 (1993).
Han et al., "Urinary biomarkers in the early diagnosis of acute kidney injury", Kidney Internati., 73(7):863-869 (2008).
Yerramilli et al., "Kidney Disease and the Nexus of Chronic Kidney Disease and Acute Kidney Injury: The Role of Novel Biomarkers as Early and Accurate Diagnostics", The Veterinary Clinics of North American, Small Animal Practice, 46(6):961-993 (2016).
Database UniParc, Database Accession No. UPI0000EB0729 (May 3, 2011).
Invitation to Pay Additional Fees for corresponding PCT application No. PCT/US17/020377, dated Jun. 20, 2017.
Zhang et al., "Identification of novel serum biomarkers in child nephroblastoma using proteomics technology", Mol. Biol. Rep. 38:631-638 (2011).
Gursky et al., "Thermodynamic Analysis of Human Plasma Apolipoprotein C-1: High-Temperature Unfolding and Low-Temperature Oligomer Dissociation", Biochemistry, 37:1283-1291 (1998).
Dieterle et al., "Urinary clusterin, cystatin C, B2-microglobin and total protein as markers to detect drug-induced kidney injury", Nature Biotechnology, 28(5):463-469 (2010).
Bonavida et al., "Anti-Inosine Antibodies of Different Specificity Produced by Immunization with Two Immunogens", Immunochemistry, 9:445-449 (1972).
Inoye et al., "Detection of Inosine-containing Transfer Ribonucleic Acid Species by Affinity Chromatography on Columns of Anti-Inosine Antibodies", The Journal of Biological Chemistry, 248(23):8125-8129 (1973).
Inouye et al., "Anti-Inosine Antibodies", Biochimica Et Biophysica Acta, 240:594-603 (1971).
Fatima et al., "Effect of potassium dichromate on renal brush border membrane enzymes and phosphate transport in rats", Human & Experimental Toxicology, 24:631-638 (2005).
Nabity et al., "Day-to-Day Variation of the Urine Protein: Creatinine Ratio in Female Dogs with Stable Glomerular Proteinuria Caused by X-Linked Herediatry Nephropathy", J. Vet Intern Med, 21:425-430 (2007).
Ruegg et al., "Differential Patterns of injury to the Proximal Tubule of Renal Cortical Slices following in vitro Exposure to Mercuric Chloride, Potassium Dischromate, or Hypoxic Conditions", Toxicology and Applied Pharmacology, 90:261-273 (1987).
Tenorio-Velazquez et al., "Hypothyroidism attenuates protein tyrosine nitration, oxidative stress and renal damage induced by ischemia and reperfusion: effect unrelated to antioxidant enzymes activities", BMC Nephrology, 6:4 (2005).
Chiusolo et al., "Kidney Injury Molecule-1 Expression in Rat Proximal Tubule after Treatment with Segment-Specific Nephrotoxicants: A Tool for Early Screening of Potential Kidney Toxicity", Toxicologic Pathology, 38:338-345 (2010).
Abrahamson et al., "Isolation of Six Cysteine Proteinase Inhibitors from Human Urine", The Journal of Biological Chemistry, 261(24):11282-11289 (1986).
Hopsu-Havu et al., "Serum cysteine proteinase inhibitors with special reference to kidney failure", Scand J Clin Lab Invest, 45:11-16 (1985).
Database Geneseq [Online] Feb. 3, 2011, "Human org 32987", EBI accession No. GSP:AUN31646.
Puppione et al., "Mass spectral analysis of the apolipoproteins on dog (Canis lupus familiaris) high density lipoproteins. Detection of apolipoprotein A-II", Comparative Biochemistry and Physiology, pp. 290-296 (2008).
Assaife-Lopes et al., "Adenosine deamination to inosine in isolated basolateral membrane from kidney proximal tubule: implication for modulation of the membrane-associated protein kinase A", Archives of Biochemistry and Biophysics, 486:44-50 (2009).
Nishiyama et al., "Renal interstitial adenosine metabolism during ischemia in dogs", Am. J. Physiol. Renal Physiol., 280:F231-238 (2001).
Guinzberg et al., "Inosine released after hypoxia activates hepatic glucose liberation through A3 adenosine receptors", Am. J. Physiol. Endocrinol. Metab., 290:E940-951 (2006).
Modis et al., "Cytoprotective effects of adenosine and inosine in an in vitro model of acute tubular necrosis", Br. J. Pharmacol., 158:1565-1578 (2009).
Choi et al., "Dialysis modality-dependent changes in serum metabolites: accumlation of inosine and hypoxanthine in patients on haemodialysis", Nephrol. Dial. Transplant, 26:1304-1313 (2011).
Jerala et al., "Cloning a synthetic gene for human stefin B and its expression in E. coli", FEBS Lett. Oct. 24, 1988;239(1):414.
Labome, CSTB (CystatinB, Stefin B CST6, STFB Liver Thiol Proteinase Inhibitor, StefinB), US Biological S797286F product information, retrieved from https://www.labome.com/product/US-Biological/S7972-86F.html on May 1, 2017, 2 pages.
Grauer, "Staging and management of canine chronic kidney disease", retrieved from http://veterinarynews.dvm360.com/stagingandmanagementcaninechronickidneydisease?id=&pageID=1&sk=&date=on Feb. 12, 2016 2 pages.
Khan et al., "Expression of Cyclooxygenase-2 in Canine Renal Cell Carcinoma", Vet. Pathol. 38:116-119 (2001).
Selvarajah et al., "Gene expression profiling of canine osteosarcoma reveals genes associated with short and long survival times", Molecular Cancer, 2009, 8:72, pp. 1-8.
Anderson, "The Clinical Plasma Proteome: A Survey of Clinical Assays for Proteins in Plasma and Serum", Clinical Chemistry, 56:2, 177-185 (2010).
GenBank Accession No. XM_535601.3 dated Dec. 2, 2011.
Cowgill et al., "Is Progressive Chronic Kidney Disease a Slow Acute Kidney Injury", Vet Clin Small Anim, 46(6):995-1013 (2016).
Musante et al., "Proteases and Protease Inhibitors of Urinary Extracellular Vesicles in Diabetic Nephropathy", J Diabests Res, 2015:1-14 (2015).
Yerramilli, "Novel Kidney Biomarkers" Discovery & Future, Slides presented at IRIS Renal Week (2016).
GenBank Accession No. DR105799.1 dated Jun. 13, 2005.
GenBank Accession No. DN348706.1, dated Mar. 4, 2005.
GenBank Accession No. GR886024.1, dated Aug. 1, 2010.
International Search Report for corresponding PCT application No. PCT/US2017/020377 dated Jul. 20, 2017.
Feldman et al., "Cystatin B as a tissue and urinary biomarker of bladder cancer recurrence and disease progression", Clin. Cancer Res., 15(3):1024-31 (2009).

* cited by examiner

A: Canine Reference Range

| | |
|---|---|
| Mean | 59.757143 |
| Std Dev | 66.055464 |
| Std Err Mean | 3.947569 |
| Upper 95% Mean | 67.527945 |
| Lower 95% Mean | 51.986341 |
| N | 280 |

B. Feline Reference range

| | |
|---|---|
| Mean | 56.642857 |
| Std Dev | 67.102696 |
| Std Err Mean | 10.354171 |
| Upper 95% Mean | 77.553529 |
| Lower 95% Mean | 35.732185 |
| N | 42 |

Figure 10: Cystatin B Negative population (n=58)
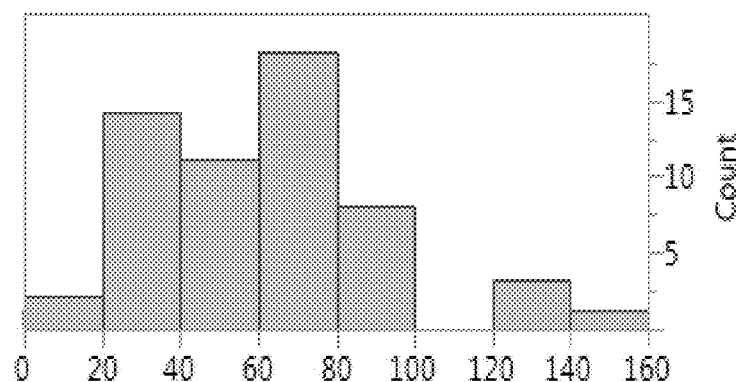
Mean: 60.927313
Std. Dev. 29.473122
Std. Err Mean 3.8700105
Upper 95% Mean 68.676875
Lower 95% Mean 53.177751
N: 58

METHODS AND COMPOSITIONS FOR THE DETECTION AND DIAGNOSIS OF RENAL DISEASE AND PERIODONTAL DISEASE

PRIORITY

This application claims the benefit of U.S. Ser. No. 62/302,299, filed on Mar. 2, 2016, which is incorporated by reference herein in its entirety.

SEQUENCE LISTING

This document incorporates by reference herein an electronic sequence listing text file, which is filed in electronic format via EFS-Web. The text file is named "16-179-WO_ST25.final.txt," is 7.10 KB, and was created on Mar. 2, 2017.

BACKGROUND

Renal disease is associated with increased water consumption, frequent urination, diminished appetite, weight loss and muscle atrophy. Generally, by the time clinical symptoms of renal disease develop, irreparable kidney damage has occurred. Early detection permits earlier treatment and in turn slows disease progression. Current treatment includes dialysis and a diet low in phosphorous and protein. Early detection is crucial for improved life span and quality of life.

In mammals, renal disease progression is divided into five levels. Current methods for detecting renal disease in mammals, e.g., canines, include kidney ultrasound, biopsy, or measurement of urine protein/creatinine levels. Biopsy is invasive and creatinine measurement is not accurate until stage three of renal failure, which is after significant tissue damage has occurred. Methods for detecting renal disease at earlier stages are needed in the art so that disease progression can be halted.

SUMMARY

One embodiment provides a method for detecting cystatin B ("Cys B") polypeptides in a sample. The method comprises contacting the sample with one or more antibodies that specifically bind one or more polypeptides consisting of (or comprising) SEQ ID NOs:1, 2, 3, 4, 5, 6, 7, 8, 9, 10, 11, 12, 13, 14, 15, 16, 17, 18, 19, 20, 21, 22, 23, 24, 25, 26, or 27 under conditions suitable for formation of complexes of the cystatin B polypeptides and the one or more antibodies that specifically bind one or more polypeptides consisting of (or comprising) SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27. Complexes of cystatin B polypeptides and the one or more antibodies that specifically bind one or more polypeptides consisting (or comprising) of SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27 are detected.

Another embodiment provides a method for diagnosing renal disease in a subject. The method comprises determining the amount of cystatin B polypeptides in a sample from the subject, wherein the amount of the cystatin B polypeptides is determined using one or more antibodies that specifically bind one or more polypeptides consisting (or comprising) of SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27. The amount of the cystatin B polypeptides in the sample is compared to a control sample or control standard, wherein elevated levels of cystatin B polypeptides in the sample compared to the control sample or control standard is an indication of renal disease.

Yet another embodiment provides a method for treating a disease condition in a subject. The method comprises requesting a test providing the results of an analysis to determine the amount of cystatin B polypeptides in a sample from the subject using one or more antibodies that specifically bind one or more polypeptides consisting (or comprising) of SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27. Treatment for decreased renal function is administered to the subject if the sample contains an elevated amount of cystatin B polypeptides as compared to a control sample or control standard for the disease condition. The disease condition can be acute kidney injury or active kidney injury in a chronic kidney disease patient, acute kidney injury, active kidney injury, progressive chronic kidney disease, periodontal disease, upper urinary tract infections, renal disease, or a combination thereof.

Still another embodiment provides a method for diagnosing periodontal disease in a subject. The method comprises determining the amount of a cystatin B polypeptides in a sample from the subject, wherein the amount of the cystatin B polypeptides is determined using one or more antibodies that specifically bind one or more polypeptides consisting of (or comprising) SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27. The amount of the cystatin B polypeptides in the sample is compared to a control sample or control standard, wherein elevated levels of cystatin B polypeptides in the sample compared to the control sample or control standard is an indication of periodontal disease in the subject.

Another embodiment provides a method of differentiating upper urinary tract infections from lower urinary tract infections. The method comprises determining the amount of cystatin B polypeptides in a sample from the subject, wherein the amount of the cystatin B polypeptides is determined using one or more antibodies that specifically bind one or more polypeptides consisting of (or comprising) SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27. The amount of the cystatin B polypeptides in the sample is compared to a control sample or control standard, wherein elevated levels of cystatin B polypeptides in the sample compared to the control sample or control standard is an indication of an upper urinary tract infection in the subject.

Another embodiment provides a method of differentiating acute kidney injury from lower urinary tract infections. The method comprises (a) determining the amount of cystatin B polypeptides in a sample from the subject, wherein the amount of the cystatin B polypeptides is determined using one or more antibodies that specifically bind one or more polypeptides consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27, and (b) comparing the amount of the cystatin B polypeptides in the sample to a control sample or control standard, wherein elevated levels of cystatin B polypeptides in the sample compared to the control sample or control standard is an indication of acute kidney injury in the subject.

In an embodiment renal disease can be caused by chronic kidney disease, acute kidney injury, or bacterial infection. In one embodiment, the renal disease, chronic kidney disease, or acute kidney injury is not caused by cancer. The bacterial infection can be caused by *Anaplasma* sp., *Ehrlichia* sp., *Leptospira* sp., *Escherichia* sp. or *Borrelia* sp. The amount of the cystatin B polypeptides can be determined by detecting complexes of cystatin B polypeptides and the one or more antibodies specific for one or more polypeptides consisting (or comprising) of SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27.

In one embodiment complexes of cystatin B polypeptides and one or more antibodies specific for one or more polypeptides consisting of (or comprising) SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27, can be contacted with an indicator agent prior to detection. The one or more antibodies can specifically bind one or more polypeptides consisting of (or comprising) SEQ ID NO: 5, 6, 7, 11, or 13.

In an embodiment the subject can be a non-human animal and the sample can be blood, serum, plasma, urine, saliva, plaque, crevicular fluid, gingival biopsy, or tongue swab.

In an embodiment, the cystatin B polypeptides or amount of cystatin B polypeptides can be determined by an immunoassay, a competitive immunoassay, a sandwich immunoassay, an enzyme-linked immunosorbent assay (ELISA), a radioimmunoassay (RIA), a turbidimetric immunoassay, a particle-enhanced turbidimetric immunoassay, or a western blot assay, Yet another embodiment provides an isolated antibody that specifically binds to one or more polypeptides consisting of (or comprising) SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27. The isolated antibody can be lyophilized; conjugated to a label; immobilized to a solid support; specifically bound to a polypeptide consisting of (or comprising) SEQ ID NO:1, 2, 3, 4, 5, 6, 7, 8, 9, 10, 11, 15, 16, 17, 18, 19, 20, 21, 22, 23, 24, 25, 26, or 27; or immobilized to a solid support and specifically bound to a polypeptide consisting of (or comprising) SEQ ID NO:1, 2, 3, 4, 5, 6, 7, 8, 9, 10, 11, 15, 16, 17, 18, 19, 20, 21, 22, 23, 24, 25, 26, or 27.

In an embodiment, the antibodies can be immobilized to a solid support and can be conjugated to one or more labels.

Still another embodiment provides a kit for diagnosing kidney disease, acute kidney injury or active kidney injury in a chronic kidney disease patient, active kidney injury, progressive chronic kidney disease, acute kidney injury, upper urinary tract infection, or periodontal disease. The kit can comprise one or more antibodies that specifically bind to one or more polypeptides consisting of (or comprising) SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27; and one or more reagents that facilitate binding of the one or more antibodies to cystatin B polypeptides present in a subject sample.

Another embodiment provides one or more isolated polypeptides consisting of (or comprising) SEQ ID NOs:1, 2, 3, 4, 5, 6, 7, 8, 9, 10, 11, 12, 13, 15, 16, 17, 18, 19, 20, 21, 22, 23, 24, 25, 26, or 27. The polypeptides can be lyophilized; conjugated to a label; immobilized to a solid support; or specifically bound to one or more antibodies that specifically bind one or more polypeptides consisting of (or comprising) SEQ ID NOs:1, 2, 3, 4, 5, 6, 7, 8, 9, 10, 11, 12, 13, 14, 15, 16, 17, 18, 19, 20, 21, 22, 23, 24, 25, 26, or 27.

Yet another embodiment provides a method for diagnosing renal disease in a mammalian subject, such as a human, canine, or feline subject. The method comprises (a) determining the amount of cystatin B polypeptides in a sample (e.g. urine, blood, plasma, serum, cells, tissue); and (b) comparing the amount of the cystatin B polypeptides in the sample to a control sample or control standard, wherein elevated levels of cystatin B polypeptides in the sample compared to the control sample or control standard is an indication of renal disease. The amount of cystatin B polypeptides can be determined using an isolated antibody that specifically binds to one or more polypeptides consisting of (or comprising) SEQ ID NOs: 1, 2, 3, 4, 5, 6, 7, 8, 9, 10, 11, 12, 13, 14, 15, 16, 17, 18, 19, 20, 21, 22, 23, 24, 25, 26, or 27. The renal disease in the mammal can be, for example, acute kidney injury or active kidney injury in a chronic kidney disease patient, chronic kidney disease, progressive chronic kidney disease, acute kidney injury, active kidney injury, upper urinary tract infections, or bacterial infection of kidneys. In an embodiment, the renal disease is not cancer or renal cancer.

An embodiment provides an immunocomplex comprising (i) one or more isolated antibodies that specifically bind to one or more polypeptides consisting of SEQ ID NOs: 1, 2, 3, 4, 5, 6, 7, 8, 9, 10, 11, 12, 13, 15, 16, 17, 18, 19, 20, 21, 22, 23, 24, 25, 26, or 27 and (ii) one or more polypeptides that are specifically bound to the one or more isolated antibodies. The one or more polypeptides can be, for example, SEQ ID NOs: 1, 2, 3, 4, 5, 6, 7, 8, 9, 10, 11, 12, 13, 15, 16, 17, 18, 19, 20, 21, 22, 23, 24, 25, 26, 27, or combinations thereof. An immunocomplex is a complex formed between an antigen (such as a polypeptide) and an antibody. The immunocomplex can be immobilized to a solid support.

Specific embodiments will become evident from the following more detailed description of certain preferred embodiments and the claims.

BRIEF DESCRIPTION OF THE DRAWINGS

FIG. 10 shows Cys B values in serum from the healthy canines.

Figure 1:
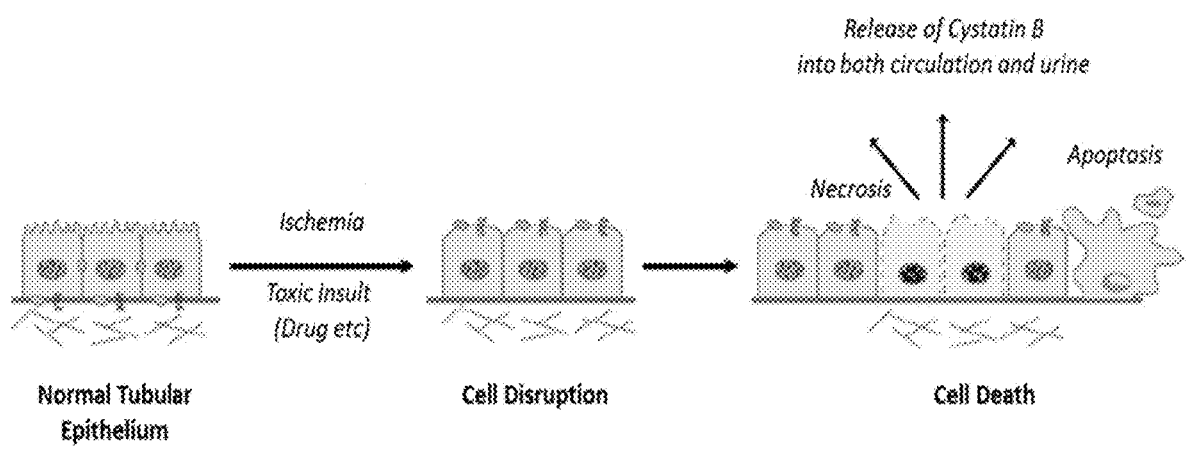
FIG. 1 shows normal tubular epithelium, cell disruption, and cell death in epithelial cells of the proximal tubule.

These and other objects and features will be better understood from the following detailed description taken in conjunction with the drawings wherein:

DETAILED DESCRIPTION OF THE INVENTION

This invention is more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

The terms used in the specification generally have their ordinary meanings in the art, within the context of the compositions and methods described herein, and in the specific context where each term is used. Some terms have been more specifically defined below to provide additional guidance to the practitioner regarding the description of the compositions and methods.

Compositions and methods described herein can be used to prognose, diagnose, and monitor progression of several diseases and conditions, including for example, kidney disease, acute kidney injury or active kidney injury in a chronic kidney disease patient, progressive chronic kidney disease, acute kidney injury, active kidney injury, upper urinary tract infections, and periodontal disease. Kidney disease includes any disease conditions that result in (1) decreased kidney function as compared to healthy subjects; or (2) physical damage to the kidneys; or (3) both. In one embodiment kidney disease does not include cancer or does not include renal cancer. Markers for cancer including renal cancer can be different from those for acute kidney injury or active kidney injury in a chronic kidney disease patient, chronic kidney disease, progressive chronic kidney disease, active kidney injury, acute kidney injury, upper urinary tract infections, or periodontal disease. In one embodiment the acute kidney injury in a chronic kidney disease patient, progressive chronic kidney disease, active kidney injury, acute kidney injury, upper urinary tract infections, or periodontal disease does not include cancer or does not include renal cancer.

Chronic kidney disease (CKD) is a condition characterized by a gradual loss of kidney function over time. CKD is also known as chronic renal disease. CDK does not include kidney cancer, renal cell carcinoma, bladder cancer or other cancers. As CKD worsens, wastes can build to high levels in the blood and high blood pressure, anemia, weak bones, poor nutritional health and nerve damage can occur. CKD increases the risk of heart and blood vessel disease and can eventually lead to kidney failure. CKD can be caused by diabetes, high blood pressure and other disorders. Early detection and treatment can often keep the disease from getting worse.

The stages of CKD in canines as established by the International Renal Interest Society are shown in Table 1.

TABLE 1

| Serum Creatinine Concentration | Stage I Nonazotemic CKD | Stage II Mild renal azotemia | Stage III Moderate renal azotemia | Stage IV Severe renal azotemia |
|---|---|---|---|---|
| mg/dL | <1.4 | 1.4-2.0 | 2.1-5.0 | >5.0 |
| Mmol/L | <125 | 125-179 | 180-439 | >440 |

The stages of CKD in felines as established by the International Renal Interest Society are shown in Table 2.

TABLE 2

| Serum Creatinine Concentration | Stage I Nonazotemic CKD | Stage II Mild renal azotemia | Stage III Moderate renal azotemia | Stage IV Severe renal azotemia |
|---|---|---|---|---|
| mg/dL | <1.6 | 1.6-2.8 | 2.9-5.0 | >5.0 |
| Mmol/L | <140 | 140-250 | 251-440 | >440 |

Methods described herein can detect acute kidney injury or active kidney injury in stage 1, 2, 3, or 4 CKD. In one embodiment, the methods can detect acute kidney injury or active kidney injury in stage 1, 2, 3, or 4 CKD before creatinine assays can detect acute kidney injury or active kidney injury in stage 1, 2, 3, or 4 CKD.

Kidney disease in humans is staged according to glomerular filtration rate (GFR). A formula using the person's age, race, gender and their serum creatinine is used to calculate a GFR. Below shows the five stages of CKD and GFR for each stage:

Stage 1 with normal or high GFR (GFR>90 mL/min)

Stage 2 Mild CKD (GFR=60-89 mL/min)

Stage 3A Moderate CKD (GFR=45-59 mL/min)

Stage 3B Moderate CKD (GFR=30-44 mL/min)

Stage 4 Severe CKD (GFR=15-29 mL/min)

Stage 5 End Stage CKD (GFR<15 mL/min)

Methods described herein can detect acute kidney injury or active kidney injury in humans in stage 1, 2, 3A, 3B, 4, or 5 CKD. In one embodiment, the methods can detect acute kidney injury or active kidney injury in humans in stage 1, 2, 3A, 3B, 4, or 5 CKD before creatinine assays or GFR values can detect acute kidney injury or active kidney injury in stage 1, 2, 3A, 3B, 4, or 5 CKD.

The chronic kidney disease or renal disease can be glomerular or tubular.

Acute kidney injury (AKI) is defined as an abrupt or rapid decline in renal filtration function. AKI can lead to chronic kidney disease (CKD), kidney failure needing dialysis (end-stage kidney disease), heart disease, or death. Even mild AKI or a complete recovery from AKI may have some short- and long-lasting health problems. AKI can be caused by damage to kidney tissue from decreased renal blood flow from any cause (e.g. low blood pressure, dehydration), exposure to substances harmful to the kidney, anti-inflammatory processes in the kidneys, systemic disease, crush injuries, antibiotics, sepsis or an obstruction of the urinary tract. AKI can lead to metabolic acidosis, high potassium levels, uremia, changes in body fluid balance, and effects on other organ systems. In one embodiment AKI does not include cancer or does not include renal cancer. The grades of AKI in felines and canines as established by the International Renal Interest Society are shown in Table 3.

TABLE 3

| AKI Grade | Blood Creatinine | Clinical Description |
|---|---|---|
| Grade I | <1.6 mg/dl (<140 μmol/l) | Non Azotemic AKI: Documented AKI (historical, clinical, laboratory or imaging evidence of AKI, clinical oliguria/anuria, |

TABLE 3-continued

| AKI Grade | Blood Creatinine | Clinical Description |
| --- | --- | --- |
| | | volume responsiveness; and/or Progressive non azotemic increase in blood creatinine ≥0.3 mg/dl (≥26.4 µmol/l) within 48 hours; and/or Measured oliguria <1 ml/kg/hr) or anuria over 6 hours. |
| Grade II | 1.7-2.5 mg/dl (141-220 µmol/l) | Mild AKI: Documented AKI and static or progressive azotemia Progressive azotemic increase in blood creatinine; ≥0.3 mg/dl (≥26.4 µmol/l) within 48 hours or, volume responsiveness; Measured oliguria (<1 ml/kg/hr) or anuria over 6 hrs |
| Grade III | 2.6-5.0 mg/dl (221-439 µmol/l) | Moderate to Severe AKI: Documented AKI and increasing severities of azotemia and functional renal failure |
| Grade IV | 5.1-10.0 mg/dl (440-880 µmol/l) | |
| Grade V | >10 mg/dl (>880 µmol/l) | |

In an embodiment methods described herein can detect grade 1, 2, 3, 4, or 5 AKI. In one embodiment, the methods described herein can detect grade 1, 2, 3, 4, or 5 AKI before creatinine assays can detect grade 1, 2, 3, 4, or 5 AKI.

AKI can be staged in humans as follows:

TABLE 3A

| Stage | Creatinine | Urine Output |
| --- | --- | --- |
| 1 | 1.5-1.9 times baseline OR ≥0.3 mg/dl (≥26.5 µmol/l) increase | <0.5 ml/kg/h for 6-12 hours |
| 2 | 2.0-2.9 times baseline | <0.5 ml/kg/h for ≥12 hours |
| 3 | 3.0 times baseline OR Increase in serum creatinine to ≥4.0 mg/dl (≥353.6 µmol/l) OR Initiation of renal replacement therapy OR in patients <18 years, decrease in eGFR to <35 ml/min per 1.73 m² | <0.3 ml/kg/h for ≥24 hours OR Anuria for ≥12 hours |

In an embodiment methods can detect stage 1, 2, or 3 AKI in humans. In one embodiment, the methods can detect stage 1, 2, or 3 AKI in humans before creatinine assays can detect stage 1, 2, or 3 in humans.

In one embodiment kidney disease, CKD, or AKI is caused by bacterial infection. In one embodiment the bacterial infection is caused by *Anaplasma* sp., *Ehrlichia* sp., *Leptospira* sp., *Escherichia* sp. or *Borrelia* sp.

Active kidney injury has been defined as an ongoing or progressive kidney injury, kidney disorder or kidney pathology. Active kidney injury generates cumulative damage to the kidney.

Polypeptides

Cystatins A & B are members of family 1 of the Cystatin superfamily and are relatively small proteins with around 11 kDa in size. In humans, these proteins are monomeric and about 11 kDa in size. They are not glycosylated and do not have the disulphide bridges seen in other Cystatin superfamilies. They also lack signal sequences and so are generally intra-cellular proteins confined to the cell. See, Ochieng & Chaudhuri, J Health Care Poor Underserved 2010, 21(1 Suppl):51. Some amount of cystatin B is present in extracellular fluids and it has been purified from human urine. See, Abrahamson et al., J Biol Chem 1986, 261:11282-11289. Cystatin B has been shown to inhibit members of the lysosomal cysteine proteinases, cathepsin family, specifically cathepsin B, H and L. See, Green et al., Biochem J 1984 218:939; D'Amico et al., J Transl Med 2014, 12:350; Jarvinen & Rinne, Biochim Biophys Acta 1982, 708:210-217.

Cystatin B polypeptides are described in detail in Example 1 and include:

```
                                             (SEQ ID NO: 1)
QVKAQLEERENKKYTTFKAVTFRSQVVAGTPYFIKVQVDDDEFVHLRVFQ

SLPHENKPLALSSYQTNKAKHDELAYF (SEQ ID NO: 2)
MMCGAPSASQPATADTQAIAD (SEQ ID NO: 3)
MMCGAPSASQPATADTQAIADQVKAQLEERENKKYTTFKAVTFRSQVVAG

TXYFIKVQVDDDEFVHLRVFQSLPHENKPLALSSYQTNKAKHDELAYF (wherein the X can be any amino acid or wherein X
can be P or N).

(SEQ ID NO: 4)
QTNKAKHDELAYF Cystatin B C Terminal "Peptide 9"

(SEQ ID NO: 5)
CGAPSASQPATADTQAIA Cystatin B N-terminal "Peptide
3-20"

(SEQ ID NO: 6)
CGAPSASQ Cystatin B N-terminal "Peptide 3-10"

(SEQ ID NO: 7)
CAIADQVKA Cystatin B N-terminal "Peptide 18-25"

(SEQ ID NO: 8)
FQSLPHENKPLALSS Cystatin B "Peptide 2"

(SEQ ID NO: 9)
SQVVAGTPYFIKVQVDDD Cystatin B "Peptide 1"

(SEQ ID NO: 10)
KHDELAYF (SEQ ID NO: 11)
MMCGAPSASQPATADTQAIADQVKAQLEE (SEQ ID NO: 12)
AIADQVKA
```

-continued (SEQ ID NO: 13)
SQVVAGTNYFIKVQVDDD

One embodiment provides a purified polypeptide comprising SEQ ID NOS:1-27 or a fragment thereof. A polypeptide fragment of SEQ ID NOs:1-27 can consist of less than about 95, 90, 80, 70, 60, 50, 40, 35, 30, 25, 20, 15, 10 (or any range between about 10 and about 95) contiguous amino acids. In one embodiment a polypeptide fragment consists of more than about 10, 15, 20, 25, 30, 35, 40, 50, 60, 70, 80, 90, or 95 contiguous amino acids of SEQ ID NOs:1-27. In one embodiment, a polypeptide or fragment thereof is non-naturally occurring.

The fact that polypeptides SEQ ID NOs:1-2, 4-13, and 15, 16, 17, 18, 19, 20, 21, 22, 23, 24, 25, 26, 27, and 27 are smaller than full length Cys B polypeptides is important because smaller polypeptides can have greater specificity and/or sensitivity than full length polypeptide assays. These smaller polypeptides can be less expensive to manufacture, and may be obtained at greater purity than full length polypeptides. Additionally, the smaller fragments and the levels of smaller fragments present in a sample can be indicative of disease state. The increased levels of fragmented polypeptides (i.e., less than full length) can be a marker for disease.

A polypeptide is a polymer of three or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure.

The term "polypeptides" can refer to one or more of one type of polypeptide (a set of polypeptides). "Polypeptides" can also refer to mixtures of two or more different types of polypeptides (i.e., a mixture of polypeptides that includes but is not limited to full-length protein, truncated polypeptides, or polypeptide fragments). The terms "polypeptides" or "polypeptide" can each also mean "one or more polypeptides."

A polypeptide variant or differs by about, for example, 1, 2, 3, 4, 5, 6, 7, 8, 9, 10, or more amino acid residues (e.g., amino acid additions, substitutions or deletions) from a polypeptide shown in SEQ ID NOs:1-27 or a fragment thereof. Where this comparison requires alignment, the sequences are aligned for maximum homology. The site of variation can occur anywhere in the polypeptide.

Variant polypeptides can generally be identified by modifying one of the polypeptide sequences described herein, and evaluating the properties of the modified polypeptide to determine if it is a biological equivalent. A variant is a biological equivalent if it reacts substantially the same as a polypeptide described herein in an assay such as an immunohistochemical assay, an enzyme-linked immunosorbent Assay (ELISA), a turbidimetric immunoassay, a particle-enhanced turbidimetric immunoassay, a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide described herein to a corresponding reactive antigen or antibody by about 80, 95, 99, or 100%. An antibody that specifically binds a corresponding polypeptide also specifically binds the variant polypeptide.

Variant polypeptides are at least about 80%, or about 81, 82, 83, 84, 85, 86, 87, 88, 89, 90, 91, 92, 93, 94, 95, 96, 97, 98, or 99% identical to the polypeptide sequences shown in SEQ ID NOs:1-27. For example, a variant polypeptide of SEQ ID NOs:1-27 can be about at least 99.5%, 99%, 98%, 97%, 96%, 95%, 94%, 90%, 87%, 84%, or 81% identical to SEQ ID NOs:1-27. Variant polypeptides have one or more conservative amino acid variations or other minor modifications and retain biological activity, i.e., are biologically functional equivalents to SEQ ID NOs1-27. A biologically active equivalent has substantially equivalent function when compared to the corresponding polypeptide.

Methods of introducing a mutation into an amino acid sequence are well known to those skilled in the art. See, e.g., Ausubel (ed.), Current Protocols in Molecular Biology, John Wiley and Sons, Inc. (1994); Maniatis et al., Molecular Cloning: A Laboratory Manual, Cold Spring Harbor laboratory, Cold Spring Harbor, N.Y. (1989)). Mutations can also be introduced using commercially available kits such as "QuikChange™ Site-Directed Mutagenesis Kit" (Stratagene). The generation of a functionally active variant polypeptide by replacing an amino acid that does not influence the function of a polypeptide can be accomplished by one skilled in the art.

The variant polypeptides can have conservative amino acid substitutions at one or more predicted non-essential amino acid residues. A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. In one embodiment a polypeptide has about 1, 2, 3, 4, 5, 10, 20 or less conservative amino acid substitutions.

As used herein, percent identity of two amino acid sequences (or of two nucleic acid sequences) is determined using the algorithm of Karlin and Altschul (PNAS USA 87:2264-2268, 1990), modified as in Karlin and Altschul, PNAS USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res. 25:3389-3402, 1997). When utilizing BLAST and GappedBLAST programs the default parameters of the respective programs (e.g., XBLAST and NBLAST) are used to obtain nucleotide sequences homologous to a nucleic acid molecule described herein.

Identity or identical means amino acid sequence similarity and has an art recognized meaning. Sequences with identity share identical or similar amino acids. Sequence identity is the percentage of amino acids identical to those in the antibody's original amino acid sequence, determined after the sequences are aligned and gaps are appropriately introduced to maximize the sequence identity as necessary. Thus, a candidate sequence sharing 85% amino acid sequence identity with a reference sequence requires that, following alignment of the candidate sequence with the reference sequence, 85% of the amino acids in the candidate sequence are identical to the corresponding amino acids in the reference sequence, and/or constitute conservative amino acid changes.

A polypeptide or antibody can be covalently or non-covalently linked to an amino acid sequence to which the polypeptide or antibody is not normally associated with in nature. Additionally, a polypeptide or antibody can be covalently or non-covalently linked to compounds or molecules other than amino acids. For example, a polypeptide or antibody can be linked to an indicator reagent, an amino acid spacer, an amino acid linker, a signal sequence, a stop transfer sequence, a transmembrane domain, a protein purification ligand, or a combination thereof. In one embodiment a protein purification ligand can be one or more C amino acid residues at, for example, the amino terminus or carboxy terminus of a polypeptide. An amino acid spacer is a sequence of amino acids that are not usually associated with a polypeptide or antibody in nature. An amino acid spacer can comprise about 1, 5, 10, 20, 100, or 1,000 amino acids.

A polypeptide can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature, i.e., a heterologous amino acid sequence. A heterologous amino acid sequence can be from a different organism, a synthetic sequence, or a sequence not usually located at the carboxy or amino terminus of a polypeptide. Additionally, a polypeptide can be covalently or non-covalently linked to compounds or molecules other than amino acids, such as indicator reagents. A polypeptide can be covalently or non-covalently linked to an amino acid spacer, an amino acid linker, a signal sequence, a stop transfer sequence, a transmembrane domain, a protein purification ligand, or a combination thereof. A polypeptide can also be linked to a moiety (i.e., a functional group that can be a polypeptide or other compound) that enhances an immune response (e.g., cytokines such as IL-2), a moiety that facilitates purification (e.g., affinity tags such as a six-histidine tag, trpE, glutathione, maltose binding protein), or a moiety that facilitates polypeptide stability (e.g., polyethylene glycol; amino terminus protecting groups such as acetyl, propyl, succinyl, benzyl, benzyloxycarbonyl or t-butyloxycarbonyl; carboxyl terminus protecting groups such as amide, methylamide, and ethylamide). In one embodiment a protein purification ligand can be one or more C amino acid residues at, for example, the amino terminus or carboxy terminus or both termini of a polypeptide. An amino acid spacer is a sequence of amino acids that are not associated with a polypeptide in nature. An amino acid spacer can comprise about 1, 5, 10, 20, 100, or 1,000 amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and staphylococcal protein A, or combinations thereof. A fusion protein is two or more different amino acid sequences operably linked to each other. A fusion protein construct can be synthesized chemically using organic compound synthesis techniques by joining individual polypeptide fragments together in fixed sequence. A fusion protein construct can also be expressed by a genetically modified host cell (such as E. coli) cultured in vitro, which carries an introduced expression vector bearing specified recombinant DNA sequences encoding the amino acids residues in proper sequence. The heterologous polypeptide can be fused, for example, to the N-terminus or C-terminus of a polypeptide. More than one polypeptide can be present in a fusion protein. Fragments of polypeptides can be present in a fusion protein. A fusion protein can comprise, e.g., one or more of SEQ ID NOs:1-27, fragments thereof, or combinations thereof. Polypeptides can be in a multimeric form. That is, a polypeptide can comprise two or more copies of SEQ ID NOs:1-27 or a combination thereof.

In one embodiment, a polypeptide is derived from a human, rabbit, mouse, canine, feline, other mammal, or combinations thereof. A polypeptide can be isolated from cells or tissue sources using standard protein purification techniques. Polypeptides can also be synthesized chemically or produced by recombinant DNA techniques. For example, a polypeptide can be synthesized using conventional peptide synthesizers.

In one embodiment, a polypeptide is covalently or non-covalently immobilized to a solid phase or substrate.

A polypeptide can be produced recombinantly. A polynucleotide encoding a polypeptide can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. Polypeptides can be lyophilized, desiccated, or dried, for example freeze-dried.

Polynucleotides

An embodiment includes an isolated polynucleotide that encodes the one or more of the polypeptides disclosed herein. Polynucleotides of the invention contain less than an entire genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. In one embodiment of the invention the polynucleotides encode a polypeptide shown in SEQ ID NOs:1-27 or fragments thereof.

Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules.

Degenerate nucleotide sequences encoding polypeptides of the invention are also polynucleotides of the invention. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of polynucleotides of the invention that encode biologically functional polypeptides also are polynucleotides of the invention.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

Polynucleotides of the invention can be used, for example, as probes or primers, for example, PCR primers, to detect the presence of polynucleotides in a test sample, such as a biological sample. Probes are molecules capable of interacting with a target nucleic acid, typically in a sequence specific manner, for example, through hybridization. Primers are a subset of probes that can support an enzymatic manipulation and that can hybridize with a target nucleic acid such that the enzymatic manipulation occurs. A primer can be made from any combination of nucleotides or nucleotide derivatives or analogs available in the art that do not interfere with the enzymatic manipulation.

A probe or primer can be about 6, 7, 8, 9, 10, 11, 12, 13, 14, 15, 16, 17, 18, 19, 20, 25, 30, 40, 50, 60, 70, 80, 90, 100, 125, 150, 175, 200 or more contiguous nucleotides that encode polypeptides of the invention.

Antibodies

Antibodies include antibody molecules that specifically bind to cystatin B polypeptides described herein, variant cystatin B polypeptides described herein, or fragments thereof. An antibody can specifically bind multiple polypeptides. The term "antibodies" refers to an intact antibody or an antigen-binding portion or fragment thereof that competes with the intact antibody for antigen binding. The term "antibodies" also includes any type of antibody molecule or specific binding molecule that specifically binds one or more cystatin B polypeptides, e.g., SEQ ID NOs:1-27. An antibody can be naturally occurring, non-naturally occurring, synthetic, or genetically engineered. The terms "antigen-binding portion" of an antibody, "antigen-binding fragment" of an antibody, and the like, as used herein, include any naturally occurring, enzymatically obtainable, synthetic, or genetically engineered polypeptide, glycoprotein or immunoglobulin that specifically binds cystatin B polypeptides (e.g., SEQ ID NOs:1-27) to form a complex.

An antibody or fragment thereof binds to an epitope of a polypeptide described herein. An antibody can be made in vivo in suitable laboratory animals or in vitro using recombinant DNA techniques. Means for preparing and characterizing antibodies are well known in the art. See, e.g., Dean, Methods Mol. Biol. 80:23-37 (1998); Dean, Methods Mol. Biol. 32:361-79 (1994); Baileg, Methods Mol. Biol. 32:381-88 (1994); Gullick, Methods Mol. Biol. 32:389-99 (1994); Drenckhahn et al. Methods Cell. Biol. 37:7-56 (1993); Morrison, Ann. Rev. Immunol. 10:239-65 (1992); Wright et al. Crit. Rev. Immunol. 12:125-68 (1992). For example, polyclonal antibodies can be produced by administering a polypeptide described herein to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

An antibody can be any isotype including IgG (IgG1, IgG2, IgG2a, Ig2b, IgG3, IgG4), IgM, IgA (IgA1 and IgA2), IgD, and IgE.

An antibody can be a monoclonal antibody, a polyclonal antibody, a chimeric antibody, or antigen-binding fragments thereof. A monoclonal antibody is an antibody obtained from a group of substantially homogeneous antibodies. A group of substantially homogeneous antibodies can contain a small amount of mutants or variants. Monoclonal antibodies are highly specific and interact with a single antigenic site. Each monoclonal antibody typically targets a single epitope, while polyclonal antibody populations typically contain various antibodies that target a group of diverse epitopes. Monoclonal antibodies can be produced by many methods including, for example, hybridoma methods (Kohler and Milstein, Nature 256:495, 1975), recombination methods (U.S. Pat. No. 4,816,567), and isolation from phage antibody libraries (Clackson et al., Nature 352:624-628, 1991; Marks et al., J. Mol. Biol. 222:581-597, 1991).

Chimeric antibodies or antigen-binding portions thereof have a part of a heavy chain and/or light chain that is derived from a specific species or a specific antibody class or subclass, and the remaining portion of the chain is derived from another species, or another antibody class or subclass. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397.

Chimeric antibodies can be produced using a variety of techniques including, for example, CDR-grafting (EP 239, 400; PCT publication WO 91/09967; U.S. Pat. Nos. 5,225, 539; 5,530,101; and 5,585,089), veneering or resurfacing (EP 592,106; EP 519,596; Padlan, Molecular Immunology 28:489-498 (1991); Studnicka et al., Protein Engineering 7(6):805-814 (1994); Roguska et al., PNAS 96:969-973 (1994)), and chain shuffling (U.S. Pat. No. 5,565,332).

In one embodiment, a chimeric antibody can comprise variable and constant regions of species that are different from each other, for example, an antibody can comprise the heavy chain and light chain variable regions of one mammal, and the heavy chain and light chain constant regions from a different animal (such as mouse, rabbit, canine, feline, or human). The chimeric antibody can comprise additional amino acid acids that are not included in the CDRs introduced into the recipient antibody, nor in the framework sequences. These amino acids can be introduced to more accurately optimize the antibody's ability to recognize and bind to an antigen. For example, as necessary, amino acids in the framework region of an antibody variable region can be substituted such that the CDR of a reshaped antibody forms an appropriate antigen-binding site. See Sato et al., Cancer Res. (1993) 53:851-856.

Non-limiting examples of antigen-binding portions or fragments of antibodies include: Fab fragments; Fab' fragments, Fab'-SH fragments, F(ab')$_2$ fragments; Fd fragments; Fv fragments; single-chain Fv (scFv) molecules; sdAb fragments (nanobodies); Fab-like antibodies (an antigen-binding fragment containing variable regions of a heavy chain and light chain that is equivalent to Fab fragments that are obtained by papain digestion); F(ab')$_2$-like antibodies (an antigen-binding fragment containing two antigen-binding domains that is equivalent to F(ab')$_2$ fragments that are obtained by pepsin digestion), multispecific antibodies prepared from antibody fragments, diabody, bispecific antibody, multifunctional antibody, humanized antibody, caninized antibody, human antibody, canine antibody, feline antibody, murine antibody, rabbit antibody, synthetic antibody, CDR-grafted antibody, and minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, CDR-grafted antibodies, diabodies, triabodies, tetrabodies, minibodies, nanobodies (e.g, monovalent nanobodies, bivalent nanobodies), single-chain (Fv)$_2$ (sc(Fv)$_2$); divalent (sc(Fv)$_2$); tetravalent ([sc(Fv)$_2$]$_2$) scFV antibodies, and small modular immunopharmaceuticals (SMIPs), and shark variable IgNAR domains, are also considered "antigen-binding fragments or portions," as used herein.

"Specifically binds," "specifically bind," or "specific for" means that a first antigen, e.g., a polypeptide of SEQ ID NOs:1-27, recognizes and binds to an antibody described herein with greater affinity than to other, non-specific molecules. "Specifically binds," "specifically bind" or "specific for" also means a first antibody, e.g., an antibody raised against SEQ ID NOs:1-27, recognizes and binds to SEQ ID NOs:1-27, with greater affinity than to other non-specific molecules. A non-specific molecule is an antigen that shares no common epitope with the first antigen. Specific binding can be tested using, for example, an enzyme-linked immunosorbant assay (ELISA), a radioimmunoassay (RIA), a turbidimetric immunoassay, a particle-enhanced turbidimetric immunoassay, or a western blot assay using methodology well known in the art.

In an embodiment an antibody or antigen binding fragment thereof specifically binds to an epitope on a polypeptide set forth as SEQ ID NO:1, 2, 3, 4, 5, 6, 7, 8, 9, 10, 11, 12, 13, 14, 15, 16, 17, 18, 19, 20, 21, 22, 23, 24, 25, 26, 27, or 27. In an embodiment the epitope is AYF, LAYF (SEQ ID NO:20), ELAYF (SEQ ID NO:21), DELAYF (SEQ ID NO:22), HDELAYF (SEQ ID NO:23), KHDELAYF (SEQ ID NO:10), AKHDELAYF (SEQ ID NO:24), KAKHDELAYF (SEQ ID NO:25), NKAKHDELAYF (SEQ ID NO:26), TNKAKHDELAYF (SEQ ID NO:27), or QTNKAKHDELAYF (SEQ ID NO:4).

In one embodiment an antibody or antigen binding fragment thereof competes for binding with a second or reference antibody to SEQ ID NO:1-27 or fragments thereof. Any competitive binding assays can be used to measure competition between two antibodies to the same antigen. For example, a sandwich ELISA assay can be used for this purpose. Means of assaying for cross-reactivity are well known to those of skill in the art (see, e.g., Dowbenko et al. (1988) J. Virol. 62: 4703-4711).

A first antibody is considered to competitively inhibit binding of a second antibody, if binding of the second antibody to the antigen is reduced by at least about 30%, 40%, 50%, 60%, 75%, 90% or more, in the presence of the first antibody using any of the assays used to assess competitive binding.

Competitive binding can be ascertained by providing one or more isolated polypeptides shown in SEQ ID NOs:1-27 attached to a solid support and assaying the ability of an antibody to bind to the polypeptides or to compete with an antibody described herein for binding to the polypeptides.

Antibodies include antibodies and antigen binding fragments thereof that (a) compete for binding with a reference antibody for binding to SEQ ID NOs:1-27 or antigen binding fragments thereof; (b) binds to the same epitope of SEQ ID NOs:1-27 or antigen binding fragments thereof as a reference antibody; (c) binds to SEQ ID NOs:1-27 or antigen binding fragments thereof with substantially the same $K_d$ as a reference antibody; and/or (d) binds to SEQ ID NOs:1-27 or fragments thereof with substantially the same off rate as a reference antibody, wherein the reference antibody is an antibody or antigen-binding fragment thereof that specifically binds to a polypeptide of SEQ ID NOs:1-27 or antigen binding fragments thereof with a binding affinity $K_a$ of $10^7$ 1/mol or more.

The affinity of an antibody or antigen-binding fragment thereof for its polypeptide partner can be represented by a dissociation constant (Kd). The equilibrium dissociation constant (Kd) is calculated at the ration of $k_{off}/k_{on}$. See Chen, Y. et al., 1999, J. Mol. Biol. 293: 865-881. A variety of methods are known in the art for measuring affinity constants. In a particular embodiment, the reference antibody is an antibody or antigen-binding fragment thereof that has a binding affinity to a polypeptide of SEQ ID NOs:1-27 with a particular $K_{on}$ rate/association rate or $K_{off}$ rate. In one embodiment, the antibodies specifically bind with a $K_{on}$ of $6 \times 10^5$ $M^{-1}s^{-1}$ or better; antibodies specifically bind with a $K_{off}$ rate of $5 \times 10^{-6}$ $s^{-1}$ or better; or antibodies specifically binds with a binding affinity of 500 pM, 400 pM, 300 pM, 200 pM, 100 pM, 50 pM, 40 pM, 30 pM, 20 pM or better.

Antibodies that specifically bind SEQ ID NOs:1-27 are particularly useful for detecting the presence of cystatin B polypeptides and fragments thereof present in a sample, such as a serum, blood, plasma, cells, tissue, saliva, plaque, crevicular fluid, gingival biopsy, tongue swab, or urine sample from an animal. An immunoassay can utilize one antibody or several antibodies. An immunoassay can use, for example, a monoclonal antibody specific for one epitope, a combination of monoclonal antibodies specific for epitopes of one polypeptide, monoclonal antibodies specific for epitopes of different polypeptides, polyclonal antibodies specific for the same antigen, polyclonal antibodies specific for different antigens, or a combination of monoclonal and polyclonal antibodies. Immunoassay protocols can be based upon, for example, competition, direct reaction, or sandwich type assays using, for example, labeled antibody. Antibodies can be labeled with any type of label known in the art, including, for example, fluorescent, chemiluminescent, radioactive, enzyme, colloidal metal, radioisotope and bioluminescent labels.

Antibodies or antigen-binding fragments thereof can be bound to a support and used to detect the presence or amount of polypeptides present in samples in certain diseases and conditions. Supports include, for example, glass, polystyrene, polypropylene, polyethylene, dextran, nylon, amylases, natural and modified celluloses, polyacrylamides, agaroses and magletite. Antibodies or antigen-binding fragments thereof can be lyophilized, desiccated, or dried, for example, freeze-dried.

Antibodies can further be used to isolate polypeptides by immunoaffinity columns. The antibodies can be affixed to a solid support by, for example, absorption or by covalent linkage so that the antibodies retain their immunoselective activity. Optionally, spacer groups can be included so that the antigen binding site of the antibody remains accessible. The immobilized antibodies can then be used to specifically bind SEQ ID NOs:1-27 or fragments thereof from a biological sample, including but not limited to saliva, plaque, crevicular fluid, gingival biopsy, tongue swab, serum, blood, and urine.

Antibodies can also be used in immunolocalization studies to analyze the presence and distribution of a polypeptide described herein during various cellular events or physiological conditions. Antibodies can also be used to identify molecules involved in passive immunization and to identify molecules involved in the biosynthesis of non-protein antigens. Identification of such molecules can be useful in vaccine development. Antibodies, including, for example, monoclonal antibodies and single chain antibodies, can be used to monitor the course of amelioration of certain diseases or conditions. By measuring the increase or decrease in the amount of SEQ ID NOs:1-27 or fragments thereof in a test sample from an animal, it can be determined whether a particular therapeutic regiment aimed at ameliorating the disorder is effective. Antibodies can be detected and/or quantified using for example, direct binding assays such as RIA, ELISA, or Western blot assays.

Methods of Detection

One embodiment provides methods for detecting cystatin B polypeptides in a sample comprising contacting the sample with one or more antibodies specific for SEQ ID NOs:1-27, under conditions suitable for formation of complexes of the cystatin B polypeptides and the one or more antibodies specific for SEQ ID NOs:1-27. The complexes of cystatin B polypeptides and the one or more antibodies specific for SEQ ID NOs:1-27 are detected.

In an embodiment methods for detecting polypeptides comprising SEQ ID NOs:1-27 and fragments thereof are provided. Optionally, the amount of polypeptide comprising SEQ ID NOs:1-27 in a sample can be detected. The relative levels of the polypeptides can be used to diagnose or detect several diseases or conditions. Any method known in the art for detecting polypeptides can be used in the methods described herein.

Assay methods used in conjunction with the antibodies described herein can include direct and indirect labeling techniques, immunoaffinity columns, immunomagnetic beads, fluorescence activated cell sorting (FACS), enzyme-linked immunosorbent assays (ELISA), radioimmune assay (RIA), agglutination assays nephelometric assays, quantitative nephelometric assays, as well as labeled secondary antibodies that detect the primary antibody.

Antibodies can be detectably-labeled with, for example, fluorescent labels that have excitation and emission wavelengths adapted for detection using commercially-available instruments such as fluorescence activated cell sorters. Examples of fluorescent labels include phycoerythrin (PE), fluorescein isothiocyanate (FITC), rhodamine (RH), Texas Red (TX), Cy3, Hoechst 33258, and 4',6-diamidino-2-phenylindole (DAPI). Such labels can be conjugated to antibodies using standard techniques (Maino et al., 1995, *Cytometry* 20: 127-133).

The methods described herein can be used to detect SEQ ID NOs:1-27 or fragments thereof wherein antibodies or antigen-binding antibody fragments specifically bind SEQ ID NOs:1-27. A biological sample can include, for example, serum, blood, cells, plasma, saliva, plaque, crevicular fluid, gingival biopsy, tongue swab, or urine from a mammal such as a dog, cat or human. The test sample can be untreated, precipitated, fractionated, separated, diluted, concentrated, or purified.

As used herein, a "patient" or "subject" can mean a human or non-human animal including feline, bovine, porcine, equine, or canine.

The term "sample," "test sample," "patient sample," or "subject sample" as used herein includes but is not limited to a blood, serum, plasma, saliva, plaque, crevicular fluid, gingival biopsy, tongue swab, or urine sample obtained from a subject.

Assays include, but are not limited to those based on competition, direct reaction or sandwich-type assays, including, but not limited to enzyme linked immunosorbent assay (ELISA), western blot, IFA, radioimmunoassay (RIA), hemagglutination (HA), turbidimetric immunoassay, particle-enhanced turbidimetric immunoassay, fluorescence polarization immunoassay (FPIA), and microtiter plate assays (any assay done in one or more wells of a microtiter plate). One assay comprises a reversible flow chromatographic binding assay, for example a SNAP® assay. See e.g., U.S. Pat. No. 5,726,010.

Assays can use solid phases or substrates or can be performed by immunoprecipitation or any other methods that do not utilize solid phases. Where a solid phase or substrate is used, one or more polypeptides or antibodies are directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). In one embodiment a substrate is sintered, fine particles of polyethylene, commonly known as porous polyethylene, for example, 10-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing antibodies on solid phases include ionic, hydrophobic, covalent interactions and the like.

In one embodiment methods comprise contacting a test sample with one or a plurality of antibodies that specifically bind to SEQ ID NOs:1-27 under conditions that allow polypeptide/antibody complexes, i.e., immunocomplexes, to form. That is, antibodies specifically bind to one or a plurality of polypeptides of SEQ ID NOs:1-27 located in the sample. One of skill in the art is familiar with assays and conditions that are used to detect antibody/polypeptide complex binding. The formation of a complex between polypeptides and antibodies in the sample is detected. The formation of antibody/polypeptide complexes is an indication that polypeptides are present in the patient sample.

In one embodiment, a polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The methods can optionally comprise a positive or negative control. A positive control can contain one or more polypeptides, which will specifically bind to antibodies specific for Cys B and provide a positive result. A negative control does not contain any Cys B polypeptides or any polypeptides or other components that would specifically bind or cross-react with antibodies specific for Cys B.

In one embodiment, one or more antibodies are covalently or non-covalently immobilized to a solid phase or substrate. A sample potentially comprising a Cys B polypeptide is added to the substrate. One or more antibodies specific for Cys B are added to the substrate. The antibodies can be the same antibodies used on the solid phase or can be from a different source or species and can be linked to an indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

In another embodiment, one or more antibodies are immobilized to a solid phase or substrate. A test sample potentially containing a Cys B polypeptide is added to the substrate. Second anti-species antibodies that specifically bind Cys B polypeptides are added. These second anti-species antibodies are from a different species than the antibodies immobilized to the solid phase. Third anti-species antibodies are added that specifically bind the second anti-species antibodies and that do not specifically bind the antibodies immobilized to the solid phase are added. The third anti-species antibodies can comprise an indicator reagent such as an enzyme conjugate. Wash steps can be performed prior to each addition. A chromophore or enzyme substrate is added and color is allowed to develop. The color reaction is stopped and the color can be quantified using, for example, a spectrophotometer.

In one embodiment, one or more capture antibodies can specifically bind to one or more epitopes of a polypeptide described herein. The capture antibody or antibodies can be used to immobilize one or a plurality of polypeptides of SEQ ID NOs:1-27 to, for example a solid support. One or more detection antibodies can specifically bind to the same one or more epitopes or different one or more epitopes of the polypeptides. The detection antibody can be used to detect or visualize the immobilization of the polypeptide to a solid support. This embodiment is advantageous because it is more specific and more sensitive than assays using only one antibody for both capture and detection functions.

In one type of assay format, one or more antibodies can be coated on a solid phase or substrate. A test sample suspected of containing polypeptides comprising SEQ ID NO:1-27 or fragments thereof is incubated with an indicator reagent comprising a signal generating compound conjugated to an antibodies or antibody fragments specific for said polypeptides for a time and under conditions sufficient to form antigen/antibody complexes of either antibodies of the solid phase to the test sample polypeptides or the indicator reagent compound conjugated to an antibody specific for the polypeptides. The binding of the indicator reagent conjugated to anti-polypeptide antibodies to the solid phase can be quantitatively measured. A measurable alteration in the signal compared to the signal generated from a control sample or control standard indicates the presence of polypeptides comprising SEQ ID NOs:1-27 or fragments thereof. This type of assay can quantitate the amount of polypeptide in a test sample.

In another type of assay format, one or more antibodies are coated onto a support or substrate. An antibody is conjugated to an indicator reagent and added to a test sample. This mixture is applied to the support or substrate. If Cys B polypeptides are present in the test sample, they will bind the one or more antibodies conjugated to an indicator reagent and to the one or more antibodies immobilized on the support. The polypeptide/antibody/indicator complex can then be detected. This type of assay can quantitate the amount of polypeptide in a test sample.

In another type of assay format, one or more antibodies are coated onto a support or substrate. The test sample is applied to the support or substrate and incubated. Unbound components from the sample are washed away by washing the solid support with a wash solution. If polypeptides comprising SEQ ID NOs:1-27 or fragments thereof are present in the test sample, they will bind to the antibody coated on the solid phase. This polypeptide/antibody complex can be detected using a second anti-species specific antibody that is conjugated to an indicator reagent. The polypeptide/antibody/anti-species antibody indicator complex can then be detected. This type of assay can quantitate the amount of polypeptides in a test sample.

The formation of a polypeptide/antibody complex or a polypeptide/antibody/indicator complex can be detected by, for example, radiometric, colorimetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

The phrase "determining the amounts" as used herein refers to measuring or identifying the levels of one or more polypeptides in a sample. This can be accomplished by methodology well known in the art for the detection of polypeptides including using antibodies including, for example enzyme-linked immunosorbant assay (ELISA), a radioimmunoassay (RIA), a turbidimetric immunoassay, a particle-enhanced turbidimetric immunoassay, or a western blot assay, or immunohistochemistry. Alternatively polypeptides of SEQ ID NOs:1-27, can be determined by mass spectrometry or similar methods known by one of skill in the art. Determining the amount of polypeptide present in a sample is accomplished by such in vitro analysis and experimental manipulation.

Methods of Diagnosis

One embodiment provides methods for diagnosing renal disease in a subject. The methods comprise determining the amount of cystatin B polypeptides in a sample from the subject, wherein the amount of the cystatin B polypeptides is determined using one or more antibodies specifically bind SEQ ID NOs:1-27. The amount of cystatin B polypeptides in the sample is compared to a control sample or control standard, wherein elevated levels of cystatin B polypeptides in the sample compared to the control sample or control standard is an indication of renal disease.

Other methods can diagnose AKI in CKD patients or AKI. In one embodiment, the methods can diagnose decreased kidney function or physical damage to the kidneys caused by cancer or renal cancer. In another embodiment, the methods can diagnose renal disease, decreased kidney function or physical damage to the kidneys caused by bacterial infection. Bacterial infection can be caused by, for example, *Anaplasma* sp., *Ehrlichia* sp., *Leptospira* sp., *Escherichia* sp. or *Borrelia* sp.

An embodiment of the invention provides a method for diagnosing or detecting renal disease, decreased kidney function, or physical damage to the kidneys caused by a bacterial infection. The method comprises determining the amount of cystatin B polypeptides in a sample from the subject, wherein the amount of the cystatin B polypeptides is determined using one or more antibodies that specifically bind one or more polypeptides consisting of SEQ ID NOs: 1, 2, 3, 4, 5, 6, 7, 8, 9, 10, 11, 12, 13, 15, 16, 17, 18, 19, 20, 21, 22, 23, 24, 25, 26, or 27. The amount of the cystatin B polypeptides in the sample is compared to a control sample or control standard, wherein elevated levels of cystatin B polypeptides in the sample compared to the control sample or control standard is an indication of renal disease, decreased kidney function, or physical damage to the kidneys caused by a bacterial infection.

As disclosed herein, polypeptides are found in higher amounts or levels in diseased subject samples as compared to control subject samples from non-diseased subjects. The relative levels of polypeptides described herein in subject samples can indicate progression of disease and disease severity. That is, in some instances, a greater amount or level of cystatin B polypeptides means a more severe disease state.

Elevated levels of cystatin B polypeptides are levels that are about 10, 20, 30, 40, 50, 60, 70, 80, 90, 100, 200, 300, 400, 500% or more greater than control samples or control standards. Elevated levels of cystatin B polypeptides are levels that are about 10 to 500% or more; about 20 to 500% or more; about 30 to 500% or more; about 40 to 500% or more; about 50 to 500% or more; about 60 to 500% or more; about 100 to 500% or more than control samples or control standards.

Elevated levels of cystatin B polypeptides can also be levels that are statistically significantly increased amounts when compared to control samples or control standards.

Elevated levels of cystatin B polypeptides can also be about 10, 20, 50, 100, 200, 300, 400, 500, 600, 700, 800, 900, 1,000, 1,500, 2,000, 3,000, 4,000, 5,000, 6,000, 7,000, 8,000, 9,000, 10,000 or more ng/ml. Control levels or control standards of cystatin B polypeptides can be about 400, 350, 300, 250, 200, 150, 100, 50, 20, 10 or less ng/ml.

Elevated levels of cystatin B polypeptides can be compared to control samples or control standards that are determined using normal control subjects who do not have any type of kidney disease or condition, bacterial infection, or periodontal disease.

In some embodiments, the level of cystatin B polypeptides in a test sample is compared the level of cystatin B in a control sample from one or more normal control subjects. Typically, the measured control level in the control sample is then compared with the cystatin B polypeptide level measured in the test sample. Alternatively, the level of cystatin B polypeptides in the test sample is compared to a previously determined or predefined control level (a "control standard"). For example, the control standard for cystatin B polypeptides of can be calculated from data, such as data including the levels of cystatin B polypeptides in control samples from a plurality of normal or healthy control subjects. The normal or healthy control subjects and the test subject under assessment can be of the same species.

Particular embodiments provide reagents and methods for identifying certain diseases or conditions in a mammal, and more particularly, in dogs, cats and humans. Certain embodiments provide methods for providing a diagnosis and prognosis for patients. Identifying Cys B polypeptides in subject samples can be an independent predictor of kidney disease or an identifier of acute kidney injury or active kidney injury in chronic kidney disease stage (e.g., stages 1-4). The methods advantageously permit diagnosis and identification of acute kidney injury in or active kidney injury in chronic kidney disease and is not influenced or confounded by patient age or body mass. Accordingly, additional embodiments are directed to using said renal patient prognosis determined using the polypeptides to select appropriate renal therapies.

Identifying Cys B polypeptides in subject samples can be an independent predictor of AKI grades (e.g., grades 1-5). The methods and compositions described herein advantageously permit diagnosis and identification of AKI stages prior to grade three and is not influenced or confounded by patient age or body mass.

Antibodies can be used in a method of the diagnosis renal disease by obtaining a test sample from an animal, e.g., a human, cat or dog suspected of suffering from renal disease. The test sample is contacted with antibodies under conditions enabling the formation of antibody-antigen complexes (i.e., immunocomplexes). One of skill in the art is aware of conditions that enable and are appropriate for formation of antigen/antibody complexes. The presence or amount of antibody-antigen complexes can be determined by methodology known in the art.

Embodiments further include methods for prognosing patient health, monitoring disease progression, and/or assessing/monitoring treatment efficacy by identifying levels of specific polypeptides in a patient sample. In one aspect, the methods can be performed at multiple time points to evaluate disease progression or treatment efficacy. In a particular embodiment, the methods may be performed at diagnosis and then at specific time points post-treatment wherein a specific therapy should result in a reduction or amelioration of disease progression.

The methods described herein can also indicate the amount or quantity of polypeptides comprising SEQ ID NOs:1-27. In a particular embodiment, the amount or quantity of certain polypeptides provides an indicator of disease stage (i.e., stages 1-4), disease progression, and/or a prognostic indicator. With many indicator reagents, such as enzyme conjugates, the amount of polypeptide present is proportional to the signal generated. Depending upon the type of test sample, it can be diluted with a suitable buffer reagent, concentrated, or contacted with a solid phase without any manipulation. For example, serum or plasma samples that previously have been diluted, or concentrated specimens such as urine, can be used to determine the presence and/or amount of polypeptide present.

Polypeptides and assays described herein can be combined with other polypeptides or assays to detect the presence of renal disease. For example, polypeptides and assays can be combined with reagents suitable for the detection or measurement of creatinine or general protein levels.

An embodiment also provides methods of differentiating upper urinary tract infections from lower urinary tract infections. Upper urinary tract infections are infections of the kidney (pyelonephritis). Lower urinary tract infections are infections of the bladder (cystitis). These conditions can be difficult to tell apart. It is advantageous for health providers to tell the difference between an upper urinary tract infection and a lower urinary tract infection because the treatments can be different. Methods are needed in the art are needed for differentiating these infections.

The methods comprise determining the amount of a cystatin B polypeptides in a sample from the subject using one or more antibodies that specifically bind SEQ ID NOs:1-27. The amount of cystatin B polypeptides in the sample are compared to a control sample or control standard, wherein elevated levels of cystatin B polypeptides in the sample compared to the control sample or control standard is an indication of an upper urinary tract infection in the subject.

An embodiment provides a method of differentiating acute kidney injury from lower urinary tract infections. These conditions can be difficult to tell apart. It is advantageous for health providers to tell the difference between acute kidney injury and a lower urinary tract infection because the treatments can be different. The method comprises determining the amount of cystatin B polypeptides in a sample from the subject, wherein the amount of the cystatin B polypeptides is determined using one or more antibodies that specifically bind one or more polypeptides consisting of SEQ ID NOs:1-27. The amount of the cystatin B polypeptides in the sample are compared to a control sample or control standard, wherein elevated levels of cystatin B polypeptides in the sample compared to the control sample or control standard is an indication of acute kidney injury in the subject.

A embodiment provides a method for diagnosing periodontitis in a subject. Periodontal disease includes gingivitis (inflammation of the gums) and periodontitis. Periodontitis is a disease of the periodontal tissues that results in attachment loss and destruction of alveolar bone. Clinical diagnosis of periodontal disease is made by the recognition of various signs and symptoms in the periodontal tissues that indicate disease. The appearance of the signs and symptoms are usually long after the onset of the disease and after considerable damage to the supporting bone and tissue has occurred. Additionally, periodontal disease often cannot be properly evaluated or treated without general anesthesia in veterinary patients. Methods of early detection of periodontal disease are needed in the art. The methods comprise determining the amount of a cystatin B polypeptides in a sample from the subject. The amount of the cystatin B polypeptides is determined using one or more antibodies specific for SEQ ID NOs:1-27. The amount of the cystatin B polypeptides in the sample is compared to a control sample or control standard, wherein elevated levels of cystatin B polypeptides in the sample compared to the control sample or control standard is an indication of periodontal disease in the subject.

Methods of Treatment.

Certain embodiments provide methods for treating a disease condition in a subject. The methods comprise requesting a test providing the results of an analysis to determine the amount of cystatin B polypeptides in a sample from the subject using one or more antibodies specific for NOs:1-13. Treatment is administered to the subject for the disease condition if the sample contains an elevated amount of cystatin B polypeptides as compared to a control sample or control standard for the disease condition.

Disease conditions include AKI, periodontal disease, upper urinary tract infections, and renal disease. In one embodiment, a disease condition is not cancer or renal caner.

Treatments for CKD, AKI, and renal disease include, for example, surgery for obstructive nephron/ureteroliths, chemotherapy for renal neoplasia, dietary management, enteric phosphate binders, antiproteinurics (e.g, angiotensin-converting enzyme inhibitors (ACEI), omega-3 fatty acids), antihypertensives (e.g. ACEI, calcium channel antagonists (CCA)), fluid therapy to correct dehydration, management of acidosis, administration of diuretics, dialysis, correction of electrolyte abnormalities, antiemetics and antacids, recombinant erythropoietin. Upper urinary tract infections can be treated with antibiotics. Periodontal disease can be treated with thorough cleaning, scaling and root planning, gum graft surgery, laser treatments, regenerative procedures (use of membranes (filters), bone grafts or tissue-stimulating proteins in the pockets), dental implants, pocket reduction procedures (folding back the gum tissue and removal of the disease-causing bacteria before securing the tissue back into place).

In an alternative embodiment, the methods described herein can be used to assess the efficacy of a composition or treatment regime (whether a composition or diet) for the amelioration of disease progression. Similarly, the methods described herein can be used for assessing a composition or treatment regimens activity on patient levels of the polypeptides comprising SEQ ID NOs:1-27.

Kits

An embodiment provides kits for performing the methods disclosed herein. In certain embodiments, the kits comprise one or a plurality of antibodies specific for one or plurality of the polypeptides comprising SEQ ID NOs:1-27. Optionally included in certain embodiments of the kits can be instructions for use, as well as secondary antibodies useful in, e.g., sandwich assays. Distinguishingly labeled antibodies can also be present in the kits, as well as reagents for labeling the antibodies.

In further embodiments, kits comprise one or plurality of antibodies that each specifically bind to one or more of polypeptides comprising SEQ ID NOs:1-27. In certain embodiments, antibodies are provided on a solid support or substrate, including without limitation chips, microarrays, beads and the like.

The kits (e.g., articles of manufacture) can be for detecting the polypeptides described herein, or protein fragment thereof in a patient sample. A kit comprises one or more antibodies and compositions for determining binding of the antibodies to full-length proteins or protein fragments described herein. A kit or article of manufacture can also comprise one or more antibodies or antibody fragments and compositions for determining binding of the antibodies or antibody fragments to polypeptides in the sample. A kit can comprise a device containing one or more polypeptides or antibodies and instructions for use of the one or more polypeptides or antibodies for, e.g., the identification of renal disease in a mammal. The kit can also comprise packaging material comprising a label that indicates that the one or more polypeptides or antibodies of the kit can be used for the identification of kidney dysfunction. Other components such as buffers, controls, and the like, known to those of ordinary skill in art, can be included in such test kits. The polypeptides, antibodies, assays, and kits of described herein are useful, for example, in the diagnosis of individual cases of renal disease in a patient.

The kits are useful for diagnosing, prognosing, or monitoring the treatment of renal disease, particularly canine, feline, and human renal disease.

The embodiments illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the embodiments claimed. Thus, it should be understood that although the present description has been specifically disclosed by embodiments, optional features, modification and variation of the concepts herein disclosed may be resorted to by those skilled in the art, and that such modifications and variations are considered to be within the scope of these embodiments as defined by the description and the appended claims.

Embodiments of the methods comprising the above-mentioned features are intended to fall within the scope of the disclosure.

EXAMPLES

The Examples that follow are illustrative of specific embodiments of the disclosure, and various uses thereof. They set forth for explanatory purposes only, and are not to be taken as limiting.

Example 1: Protein Sequences of Canine Cys B

It was previously believed that canine Cys B had a protein sequence of 77 aa as shown in SEQ ID NO:1.

(SEQ ID NO: 1)
QVKAQLEERENKKYTTFKAVTFRSQVVAGTPYFIKVQVDDDEFVHLRVFQ

SLPHENKPLALSSYQTNKAKHDELAYF

This belief, however, is not correct. MDCK cell lines were grown to confluence and the adherent cells were collected and lysed with a physiological buffer containing a detergent. After lysis, cells were spun at 10000 rpm for 30 minutes to pellet cellular debris. The supernatant was used a source of urinary specific canine Cystatin B. Using the supernatant the missing 21 aa N-terminus of canine Cys B was sequenced using trypsin digestion and LC-MS identification.

(SEQ ID NO: 2)
MMCGAPSASQPATADTQAIAD

Thus, the complete amino acid sequence of canine Cys B (FL-Cys B) was determined to be:

(SEQ ID NO: 3)
MMCGAPSASQPATADTQAIADQVKAQLEERENKKYTTFKAVTFRSQVVAG

TNYFIKVQVDDDEFVHLRVFQSLPHENKPLALSSYQTNKAKHDELAYF

Example 2: Antibodies Against Canine Cystatin B

A. Antibodies Raised Against Recombinant Proteins

Polyclonal antibodies were generated according to standard methodologies in rabbits by using recombinant proteins of SEQ ID NO:1 and SEQ ID NO:3 as immunogens. Each of the antibodies thus raised specifically bound their respective recombinant immunogens in an ELISA assay.

Monoclonal antibodies were raised according to standard methodologies in mice by using a recombinant protein having SEQ ID NO:3 as immunogen, with CPG as adjuvant. Seven monoclonal antibodies generated specifically bound their respective recombinant immunogens in an ELISA assay. A HRP-goat anti-mouse IgG H&L chain secondary antibody was used to detect monoclonal binding. All clones tested bound to plates coated with 5 ug/ml of the recombinant FL Cystatin B (SEQ ID NO: 3). Table 4 shows exemplary binding data for three of the clones.

TABLE 4

Screening of monoclonal antibodies against rFL-Cys B.
Representative serial dilutional data from 3 clones

| FL-Cys B | Cys B Monoclonals @ 10 ug/ml | | |
|---|---|---|---|
| (ug/ml) | 9A3 | 5E1 | 3H4 |
| 10 | 2.79 | 2.77 | 2.74 |
| 1 | 2.38 | 2.32 | 2.36 |
| 0.5 | 1.94 | 1.87 | 1.79 |
| 0.25 | 1.54 | 1.46 | 1.43 |
| 0.125 | 1.12 | 1.04 | 0.97 |
| 0.0625 | 0.69 | 0.62 | 0.64 |
| 0.03125 | 0.44 | 0.42 | 0.43 |
| 0 | 0.11 | 0.11 | 0.13 |

The following peptides derived from canine Cystatin B were conjugated to KLH. The conjugates were used as immunogens for antibody generation in rabbits.

Cystatin B C Terminal "Peptide 9"
(SEQ ID NO: 4)
QTNKAKHDELAYF

Cystatin B N-terminal "Peptide 3-20"
(SEQ ID NO: 5)
CGAPSASQPATADTQAIA

Cystatin B N-term inal "Peptide 3-10"
(SEQ ID NO: 6)
CGAPSASQ

-continued

```
Cystatin B N-terminal "Peptide 18-25"
                                            (SEQ ID NO: 7)
CAIADQVKA Cystatin B "Peptide 2"
                                            (SEQ ID NO: 8)
FQSLPHENKPLALSS Cystatin B "Peptide 1"
                                            (SEQ ID NO: 9)
SQVVAGTPYFIKVQVDDD
```

In addition, polyclonal and monoclonal antibodies were generated according to standard methodologies in mice by using peptides SEQ ID NO:2 (N-terminal) and SEQ ID NO:5 (Peptide 3-20) as immunogens, with Freund's adjuvant. Each of the antibodies thus raised specifically bound their respective recombinant immunogens in an ELISA assay.

Each of the antibodies thus raised specifically bound their respective peptide immunogens. For example, Table 5 below show the typical binding curves of rabbit anti-peptide polyclonal antibodies against Peptides 1, 2 and 9 to their respective immunogens. All three polyclonal antibodies bound with high affinity to their targets and can be used to form a sandwich in the Cystatin B ELISA.

TABLE 5

Binding of rabbit anti-cystatin B peptides to respective immunogens

| Ab titer | Peptide 1 | Peptide 2 | Peptide 9 |
|---|---|---|---|
| 10 | 2.55 | 4.00 | 4.00 |
| 1 | 1.00 | 3.79 | 4.00 |
| 0.5 | 0.31 | 2.15 | 3.95 |
| 0.25 | 0.08 | 0.50 | 2.41 |
| 0.125 | 0.05 | 0.11 | 0.57 |
| 0.0625 | 0.04 | 0.06 | 0.12 |
| 0 | 0.04 | 0.04 | 0.05 |

In addition, anti-Peptide 9 antibody and anti-Peptide 1 antibody specifically bound recombinant FL-Cys B (SEQ ID NO:3) and a native intracellular protein in a lysate of stimulated MDCK cells in an ELISA assay. Anti-Peptide 9 antibody was shown to specifically bind peptide KHDELAYF (SEQ ID NO:10) in a competitive ELISA assay.

SEQ ID NO:11, 12, and 13 were used to immunize rabbits according to standard methodologies. Each antibody specifically bound to their respective immunogens in an ELISA assay.

Example 3: Immunoassays for the Detection of Canine Cystatin B

A Cystatin B ELISA was developed as follows.
Solid Phase and Capture Antibody:
96 well 4BX microtiter plates are coated with 10 ug/ml affinity purified rabbit anti-Peptide 9 overnight at 4° C. Plates are washed 3× with 1×PBS, pH 7.4 containing 0.05% TWEEN® (polysorbate) 20. Plates are then blocked for 2 hours with 1×PBS, pH 7.4 containing 1% BSA. After washing, as above, the plates are dried at 37° C. under vacuum for 4 hours. Plates are then stored desiccated, at 4° C.
Preparation of Detection Antibody:
Seven monoclonal antibodies were generated from mice immunized with full length recombinant Cystatin B (rFL-Cys B)(SEQ ID NO:3). One clone (3H4) was chosen based on its binding performance to rFL Cys B, purified with Protein G, and 1.0 mg of the purified antibody was labeled with Horseradish Peroxidase (HRP) using the SMCC method and desalted to remove excess HRP. The labeled antibody was titrated and 0.25-2.0 ug/ml was used in the ELISA assays.

Cystatin B Sandwich ELISA Protocol: Serum and Urine

Cystatin B is an intracellular protein and generally not freely circulating in large concentrations. This was further confirmed by the fact that no protein was found in the supernatant collected from stressed canine kidney cells. However cystatin B was purified from ruptured canine kidney cells. Therefore any cystatin B that is detected in serum or urine likely results from the rupture and death of cells. In active kidney injury, apoptosis and necrosis of epithelial cells in the proximal tubule is likely to result in increased serum and urinary cystatin B (FIG. 1).

Figure 2:
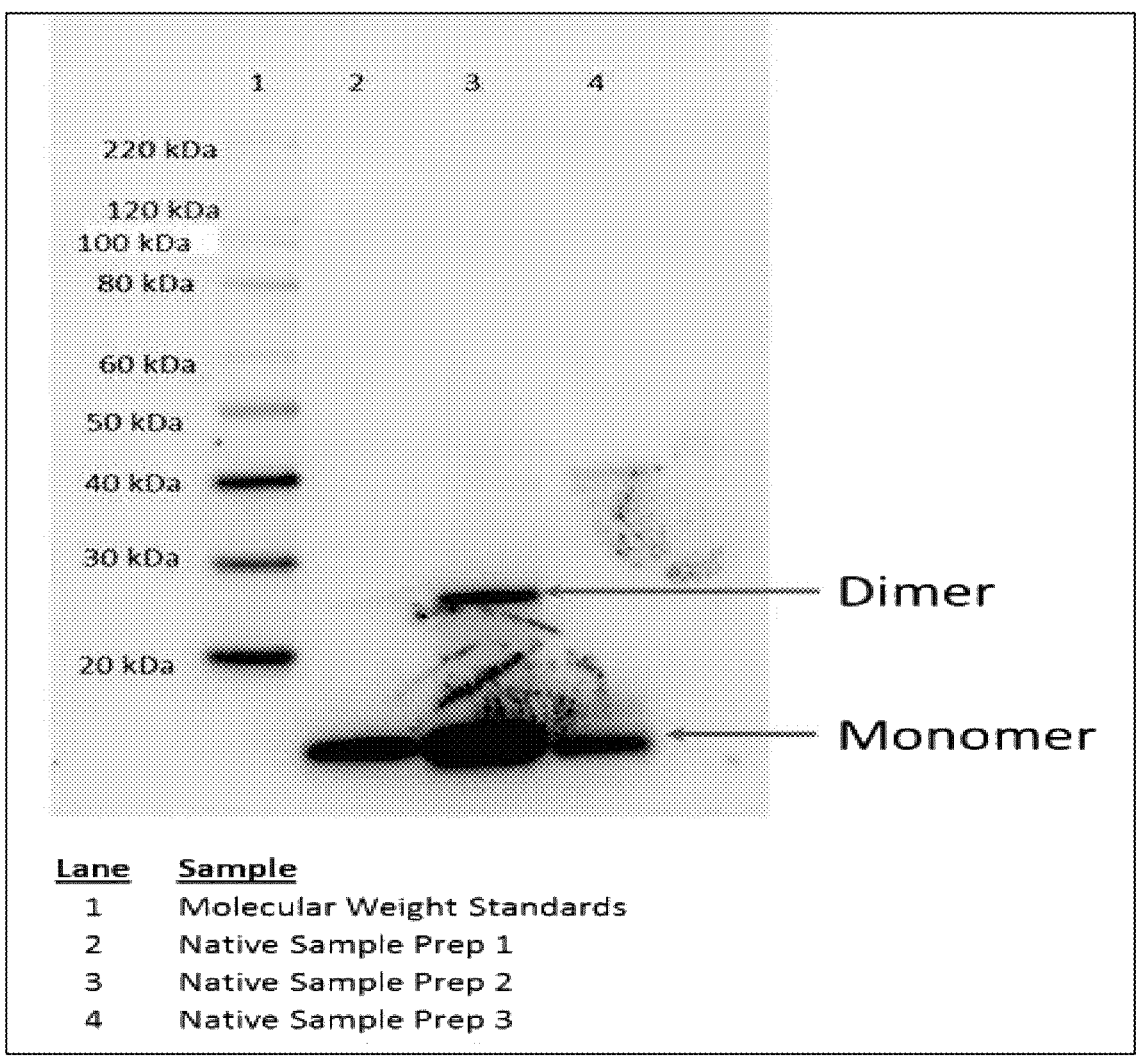
FIG. 2 shows Western blot analysis of cystatin B in the presence of cystatin C protein

Cystatin B has not been linked to kidney disease in companion animals. Monoclonal antibodies were raised against recombinant cystatin B as described above and their specificity confirmed using Western blot analysis in the presence of cystatin C protein (FIG. 2). A sandwich ELISA was also developed using these antibodies.

For a sandwich ELISA, standards were either rFL-Cys B or a detergent lysate from MDCK cell pellets. Both standard preparations were quantitated by a LCMS method. Urine samples were diluted at least 1:10 with Buffer A (0.1M PO4: pH 7.4, containing at least 0.1% Sarkosyl. Serum samples were diluted at least 1:100 in Buffer A and 100 ul was added to wells in duplicate as above. One hundred microliters (100 ul) was added in duplicate to polyclonal antibody capture wells and incubated for 1 hour, shaking at RT. Plates were then washed 6× with PETCHEK® wash (IDEXX Laboratories, Inc., Maine, USA) and 100 ul of 0.25-2 ug/ml of HRP monoclonal detection antibody was added. The detection antibody was incubated for 30 minutes shaking, followed by 6× washes, and 100 ul of substrate TMB was added to the wells. The color developed for 5 minutes followed by 100 ul of stop solution (1N HCL). Plates were read in VMAX® microplate reader. A 4PL parameter fit was used in Sigma plot to quantitated the unknowns.

Figure 3:
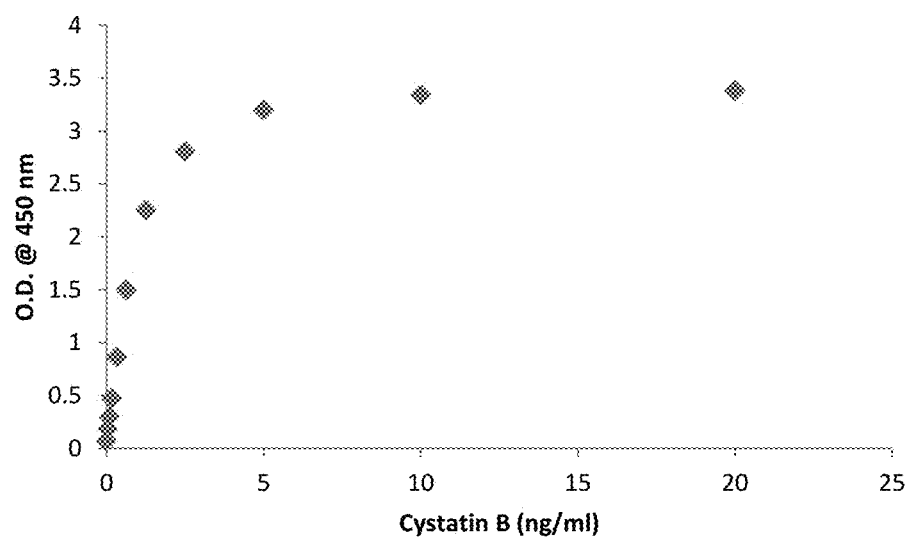
FIG. 3 shows a standard curve obtained with the Cys B ELISA assay using native canine Cystatin B (MDCK lysate).

A standard curve was obtained with the Cys B ELISA assay as described above, using native canine Cystatin B (MDCK Lysate) (FIG. 3).

Detection of Canine Cystatin B in Patient Samples

Cystatin B levels were determined in the urine of dogs, using the Cystatin B ELISA assay as described above and are shown in Table 6.

TABLE 6

Cystatin B levels in canines with kidney disease.

| Sample | Status | Cystatin B (ng/ml) |
|---|---|---|
| 1 | Healthy | 356 |
| 2 | Healthy | 382 |
| 3 | Healthy | 292 |
| 4 | AKI | 6022 |
| 5 | AKI | 7920 |
| 6 | AKI | 9559 |
| 7 | CKD | 453 |
| 8 | CKD | 1595 |
| 9 | CKD | 3372 |

As shown in Table 6, the healthy dogs had low levels of Cystatin B in their urine when compared to Acute (Active)

Kidney Injury (AKI) and Chronic Kidney Disease (CKD). AKI samples exhibited higher Cystatin B levels than CKD samples.

Figure 4:
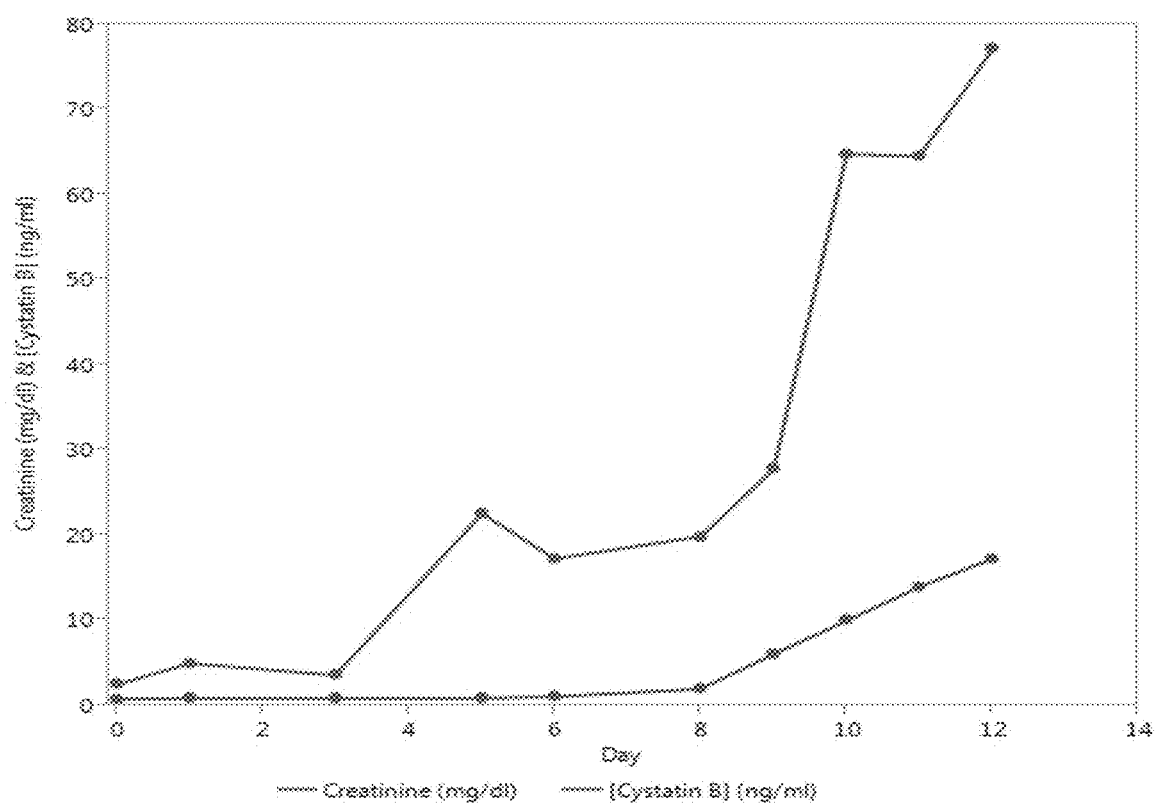
FIG. 4 shows a Cys B ELISA analysis of serum and urine from a canine gentamycin model.
Figure 5:
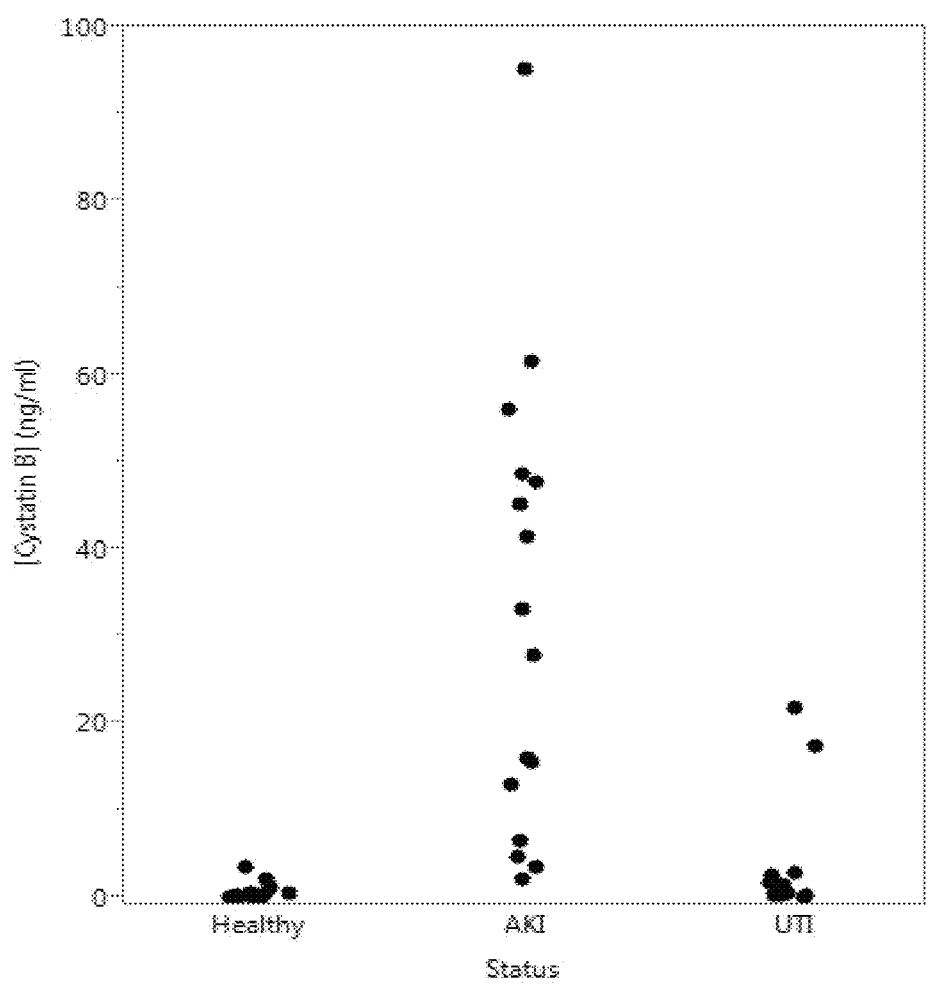
FIG. 5 shows a Cys B ELISA analysis of urine from of dogs presenting to a clinic with inflammatory or ischemic induced active kidney injury.

Cystatin B was measured using the ELISA in serum and urine from a canine gentamycin model (FIG. 4) and the urines of dogs presenting to a clinic with inflammatory or ischemic induced active kidney injury (FIG. 5). In the model system dogs were given 10 mg/kg gentamycin every 8 hours until serum creatinine reached 1.5 mg/dL. In this dog that point was reached on day 8; whereas serum cystatin B was increased over baseline on day 1. These preliminary results suggest that cystatin B is an earlier marker than creatinine for active kidney injury. In the patient samples there is a clear separation between healthy patients and those diagnosed with active kidney injury.

Example 4: Cystatin B Detection with Oral Swab

A cotton swab was used to sample the gums of a canine undergoing a dental exam. The dog presented with gingivitis, gum disease, as well as severe tooth decay. The swab was placed in a plastic test tube and stored at 4° C. until use. The swab was equilibrated to room temperature for 30 minutes then placed in 0.5 ml of Cystatin B assay buffer containing a detergent for 30 minutes. The swab was removed and was used in the Cystatin B assay as described above. A control swab without sample was used to determine background signal. The control swab was below the limit of detection (LOD) having an average OD of 0.04 while the OD of the swab from the canine undergoing extensive dental procedure was 1.04. This results in a signal to noise S/N ratio of 26. See Table 7 below:

TABLE 7

Detection of Cystatin B in an oral swab.

|  | Cystatin B (O.D @ 450 nm) | S/N |
|---|---|---|
| Control Swab | 0.04 | — |
| Canine Swab | 1.04 | 26 |

The teeth of two dogs with periodontal disease were swabbed with a cotton swab and the cystatin B was extracted in the Cystatin B ELISA buffer and run as a sample in the Cystatin B assay. A standard spiked with 1000 ng/ml recombinant full length canine cystatin B protein was run as a positive control. The signals (O.D. @ 450 nM) for recombinant full length Cystatin B protein positive control was 0.322, for Canine 1 was 1.8485, for Canine 2 was 1.444. The values for the two canines with periodontal disease were more than five times higher than the 1000 ng/ml rCanine FL-Cys B standard. Therefore, Cys B is a marker for periodontal disease in mammals such as canines.

Example 5: Modified ELISA 96 well 4BX microtiter plates were coated with 5 ug/ml affinity purified rabbit anti-Peptide 9 overnight at 4° C. Plates are washed 3× with 1×PBS, pH 7.4 containing 0.05% TWEEN® (polysorbate) 20. Plates were then blocked for 2 hours with 1×PBS, pH 7.4 containing 1% BSA. After washing, as above, the plates are dried at 37° C. under vacuum for 4 hours. Plates are then stored desiccated, at 4° C.

For a sandwich ELISA, standards were either rFL-Cys B or a detergent lysate from MDCK cell pellets. Both standard preparations were quantitated by a LCMS method. Urine samples were diluted 1:20 with Buffer A (0.1M Phosphate, pH 7.2, containing at least 1.0% N-Dodecanoyl-N-methylglycine sodium salt (Sarkosyl, Sigma)). Serum samples were diluted at least 1:50 in Buffer A and 100 ul was added to wells in duplicate as above. One hundred microliters (100 ul) was added in duplicate to polyclonal antibody capture wells and incubated for 1 hour, shaking at RT. Plates were then washed 6× with PETCHEK® wash (IDEXX Laboratories Inc., Westbrook, Me., USA) and 100 ul of 0.25-2 ug/ml of HRP-labeled monoclonal detection antibody was added. The detection antibody was incubated for 30 minutes with shaking, followed by 6× washes, and 100 ul of substrate TMB was added to the wells. The color was developed for 5 minutes followed by 100 ul of stop solution (1N HCL). Plates were read in a VMAX® microplate reader. A 4PL parameter fit was used in Sigma plot to quantitate the unknowns.

Example 6: Detection of Human Cys-B

This Example demonstrates the construction of an ELISA for detection of human Cys B using anti-canine Cys B antibodies. Recombinant Human Cystatin B (rH FL Cys B) protein (SEQ ID NO:14) was obtained from Genscript, USA.

>sp|P04080|CYTB_HUMAN Cystatin-B OS = Homo sapiens
GN = CSTB PE = 1 SV = 2
[SEQ ID NO: 14]
MMCGAPSATQPATAETQHIADQVRSQLEEKENKKEPVFKAVSEKSQVVAG

TNYFIKVHVGDEDFVHLRVFQSLPHENKPLTLSNYQTNKAKHDELTYF

Cross-reactivity of rH FL Cys B protein with antibodies raised against canine cystatin B was evaluated by sandwich ELISA. Briefly, mouse monoclonal antibodies raised against the recombinant full length canine cystatin B sequence (rC FL Cystatin B) were used a capture reagents and screened for ability to bind multiple recombinant FL Cys B antigens in a ELISA. Detection reagents screened were rabbit polyclonal N-terminal ant-canine Cystatin B antibodies and Horseradish peroxidase anti-species IgG (H&L). A series of paired reagents were found that provided a dose dependent curve in the ELISA. As shown below in Table 8, three monoclonal antibodies generated in mouse against the canine C-terminal "Peptide 9" (QTNKAKHDELAYF (SEQ ID NO:4)) (IF10, 2B5, and 9A10) paired with anti-canine N-terminal cystatin B polyclonal antibodies 327 (raised in rabbit against CAIADQVKA (SEQ ID NO:7)), 328 (raised in rabbit against CGAPSASQPATADTQAIA (SEQ ID NO:5)) or 329 (raised in rabbit against CGAPSASQ (SEQ ID NO:6)) to form a sandwich ELISA. In addition, these pairs bound Rat and Mouse rFl Cystatin B protein.

TABLE 8

Pairing of Canine reagents to form sandwich with Human, Rat, and Mouse recombinant Cystatin B protein

| Solid Phase Monoclonal | Detection Polyclonal | Canine rFL Cys B | Human rFL Cys BL | Rat rFL Cys B | Mouse rFL Cys B |
|---|---|---|---|---|---|
| IF10 mAb | 327 | 3.8 | 0.7 | 2.8 | 3.2 |
|  | 328 | 3.4 | 0.1 | 1. | 2. |
|  | 329 | 0.0 | 0.1 | 0.1 | 0.1 |
| 2B5 mAb | 327 | 3.8 | 1.0 | 3.2 | 3.5 |
|  | 328 | 3.5 | 0.3 | 2. | 3. |
|  | 329 | 0.1 | 0.1 | 0.1 | 0.1 |

TABLE 8-continued

Pairing of Canine reagents to form sandwich with Human, Rat, and Mouse recombinant Cystatin B protein

| Solid Phase Monoclonal | Detection Polyclonal | Canine rFL Cys B | Human rFL Cys BL | Rat rFL Cys B | Mouse rFL Cys B |
|---|---|---|---|---|---|
| 9A10 mAb | 327 | 3.6 | 0.6 | 2.6 | 3.5 |
|  | 328 | 3.3 | 0.1 | 1. | 3. |
|  | 329 | 0.1 | 0.2 | 0.1 | 0.2 |

Using N-terminal rabbit polyclonal antibody 327 as a solid phase capture, monoclonal mouse antibodies generated against the canine Cystatin B C-Terminal "Peptide 9" QTNKAKHDELAYF (SEQ ID NO:4) were analyzed for binding to rH FL Cystatin B. See Table 9. As shown below in Table 10, one C-terminal monoclonal antibody (9A10) formed a sandwich while another C-terminal monoclonal antibody (2B5) did not. The specificities of these monoclonal antibodies were mapped and the 9A10 monoclonal recognized a homologous sequence of both human and canine cystatin B. The 3H4 monoclonal antibody raised against rFL canine Cystatin B paired with solid phase-bound polyclonal antibody 327 showed binding both to human and canine rFL Cystatin B (Table 11).

TABLE 9

Cystatin B C-terminal Sequences

| Canine | QTNKAKHDELAYF | SEQ ID NO: 4 |
| Human | QTNKAKHDELTYF | SEQ ID NO: 15 |

TABLE 10

Epitope Mapping of Cystatin B rabbit polyclonal and mouse monoclonal antibodies.

|  | Anti-Peptide Antibodies | | |
|---|---|---|---|
|  | Polyclonal | Monoclonal | |
| Peptide Sequence | Anti-Pep 9 | 2B5 | 9A10 |
| QTNKAKHDELAYF SEQ ID NO: 4 | 3.4 | 2.5 | 2.8 |
| QTNKAKHDELAY SEQ ID NO: 16 | 3.4 | 0.2 | 2.8 |
| QTNKAKHDELA SEQ ID NO: 17 | 3.1 | 0.2 | 2A |
| QTNKAKHDEL SEQ ID NO: 18 | 2.3 | 0.1 | 0.1 |
| QTNKAKHDE SEQ ID NO: 19 | 2.3 | 0.2 | 0.1 |
| Residues Essential for Epitope |  | YF | AYF |

TABLE 11

|  |  | rFL-Cystatin B | |
|---|---|---|---|
| Capture | Conjugate | Human | Canine |
| 327 | 3H4 | 0.911 | 2.102 |
|  | 9A10 | 0.829 | 1.584 |
|  | 2B5 | 0.065 | 0.065 |
|  | 327 | 0.077 | 1.211 |

Antibodies specific for canine Cys B can be used to detect human Cys B. In particular antibodies or specific binding fragments thereof that bind to epitopes comprising AYF, LAYF (SEQ ID NO:20), ELAYF (SEQ ID NO:21), DELAYF (SEQ ID NO:22), HDELAYF (SEQ ID NO:23), KHDELAYF (SEQ ID NO:10), AKHDELAYF (SEQ ID NO:24), KAKHDELAYF (SEQ ID NO:25), NKAKHDELAYF (SEQ ID NO:26), TNKAKHDELAYF (SEQ ID NO:27), and QTNKAKHDELAYF (SEQ ID NO:4), or portions thereof can be used to detect human and canine Cys B.

Example 7: Determination of Reference Ranges in Canine and Feline Urine

Figure 6:
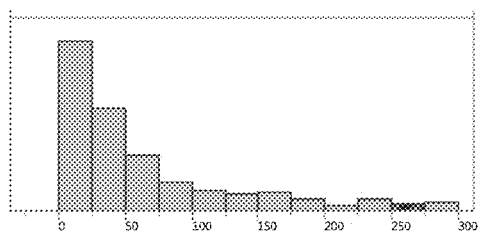
FIG. 6 panels A and B show canine and feline reference ranges.
Figure 6:
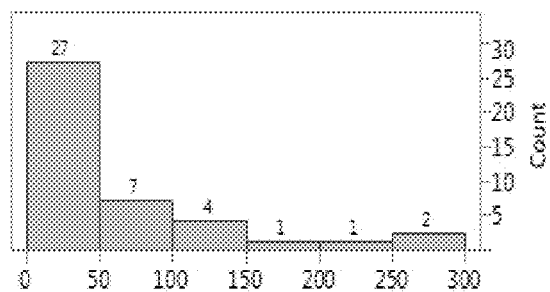

Urine samples from canines and felines were collected at a local veterinary hospital over a 2-year timeframe. Urine was aliquoted and frozen until use. Thawed urine samples were measured for Cystatin B using the ELISA assay described in Example 3. A reference range was established from healthy animals which had no indication of renal disorders upon veterinarian exam, such as serum creatinine or SDMA levels suggesting CKD, history or presentation of urinary tract stones, or urinary tract infections. Thus, a total of 280 healthy canines and 42 healthy felines were used and a reference range of 257 ng/ml was determined using the mean+3 Standard Deviations (Std Dev) for each species. See FIG. 6. Therefore, the normal, healthy range is from about 0 ng/ml to about 257 ng/ml (e.g. from about 0, 5, 10, 20, 50, 75, 100 to about 200, 210, 225, 250, or 257 ng/ml). Values above 257 ng/ml (e.g. from about 257, 260, 270, 280, 290, 300 ng/ml and above) are indicative of renal disease.

Example 8: Cystatin B in Canine AKI Population

Figure 7:
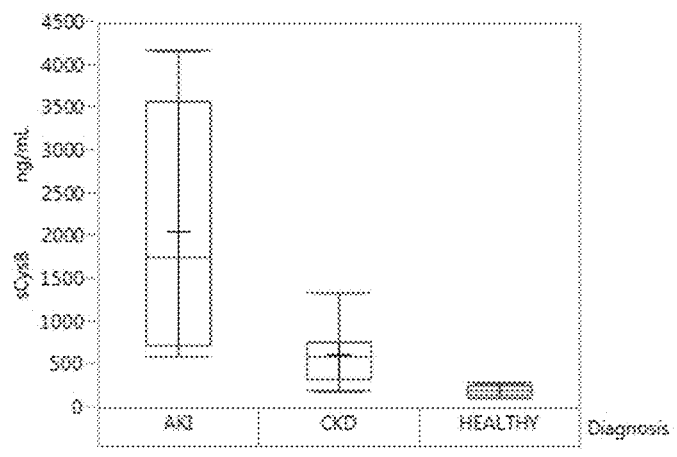
FIG. 7 panels A and B show urinary and serum Cystatin B levels significantly increased in patients diagnosed with AKI compared to healthy dogs and CKD patients.
Figure 7:
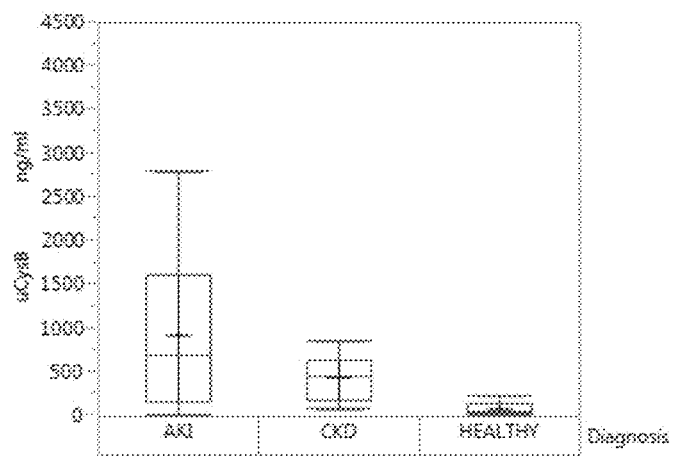

Twenty-five matched urine and serum samples from dogs with clinically confirmed AKI and healthy dogs were run in Cystatin B ELISA (Example 5). The etiology of the AKI patients included, e.g., nephrotoxic drugs, snake bites, sun stroke, ethylene glycol exposure, and infectious diseases. As shown in FIGS. 7A-B and Tables 12-13, urinary and serum Cystatin B levels significantly increased in patients diagnosed with AKI compared to healthy dogs and CKD patients.

TABLE 12

Variability Summary for sCysB ng/mL

|  | Mean | Std Dev | Std Err Mean | Lower 95% | Upper 95% | Minimum | Maximum | Range | Median | Observations |
|---|---|---|---|---|---|---|---|---|---|---|
| sCysB ng/mL | 1076.048 | 1225.574 | 267.4422 | 518.1729 | 1633.922 | 113 | 4175 | 4062 | 642 | 21 |
| Diagnosis [AKI] | 2065.625 | 1509.591 | 533.7209 | 803.5756 | 3327.674 | 604 | 4175 | 3571 | 1763 | 8 |
| Diagnosis [CKD] | 6.28 | 353.9148 | 125.1278 | 332.1198 | 923.8802 | 200 | 1348 | 1148 | 608 | 8 |
| Diagnosis [HEALTHY] | 209.6 | 67.21086 | 30.05761 | 126.1467 | 293.0533 | 113 | 291 | 178 | 206 | 5 |

TABLE 13

Variability Summary for uCysB ng/ml

|  | Mean | Std Dev | Std Err Mean | Lower 95% | Upper 95% | Minimum | Maximum | Range | Median | Observations |
|---|---|---|---|---|---|---|---|---|---|---|
| uCysB ng/ml | 525.8 | 676.3851 | 151.2443 | 209.242 | 842.358 | 14 | 2803 | 2789 | 2895 | 20 |
| Diagnosis [AKI] | 928.2857 | 1001.605 | 378.5712 | 1.955283 | 1854.616 | 14 | 2803 | 2789 | 704 | 7 |
| Diagnosis [CKD] | 449.25 | 264.6473 | 93.56696 | 227.9993 | 670.5007 | 87 | 862 | 775 | 461 | 8 |
| Diagnosis [HEALTHY] | 84.8 | 86.08833 | 38.49987 | −22.0928 | 191.6928 | 20 | 236 | 216 | 52 | 5 |

Example 9: Cystatin B in Infectious Diseases

Most infectious diseases of the urinary system in animals are aerobic bacterial infections. Common organisms include *Escherichia coli*, *Staphylococcus*, *Enterococcus*, and *Streptococcus*. Less common organisms causing infection include *Klebsiella*, *Proteus*, and *Pseudomonas*. *Mycoplasma* is an uncommon cause of urinary tract infection and is usually found as a coinfection with bacteria. Leptospirosis is a worldwide zoonotic disease caused by filamentous *Leptospira* bacteria that infect the kidney and many other organs. Rickettsial (rickettsioses) and related diseases (anaplasmosis, ehrlichiosis, Q fever, scrub typhus) are caused by a group of gram-negative, obligately intracellular coccobacilli. *Babesia*, a tickborne disease, has also been implicated in renal disease.

Serum samples from twenty canine patients confirmed positive for *Leptospira* sp. by ELISA, PCR, and Microscopic Agglutination Test (MAT) titers>1:800 (IDEXX Laboratories, Inc.) were run in the Cystatin B ELISA. Confirmed healthy canine serum samples were also run to determine the average Cystatin B level in serum. As shown below in Table 14, nine Leptospirosis positive samples (45%) were above the relative cutoff (mean+3SD) value of the serum from the healthy canines (149.1 ng/ml) (FIG. 10). This data indicates that 45% of the tested Leptospirosis patients had a kidney injury. Therefore, elevated serum levels of Cystatin B indicate the presence of kidney injury in patients infected with *Leptospira*.

TABLE 14

Cystatin B ELISA results for *Leptospira* sp. Positive samples

| Sample ID | Cystatin B (ng/ml) |
|---|---|
| 1304 | 99 |
| 2648 | 375 |
| 4282 | 241 |
| 4318 | 171 |
| 4558 | 411 |
| 4567 | 82 |
| 4628 | 133 |

TABLE 14-continued

Cystatin B ELISA results for *Leptospira* sp. Positive samples

| Sample ID | Cystatin B (ng/ml) |
|---|---|
| 4650 | 145 |
| 4873 | 767 |
| 4972 | 276 |
| 5242 | 65 |
| 5369 | 54 |
| 5529 | 292 |
| 5614 | 75 |
| 5646 | 65 |
| 5651 | 81 |
| 5659 | 203 |
| 5663 | 167 |
| 5664 | 111 |
| 5679 | 59 |
| 5694 | 141 |

Example 10: Cystatin B in Urinary Tract Infections

Figure 8:
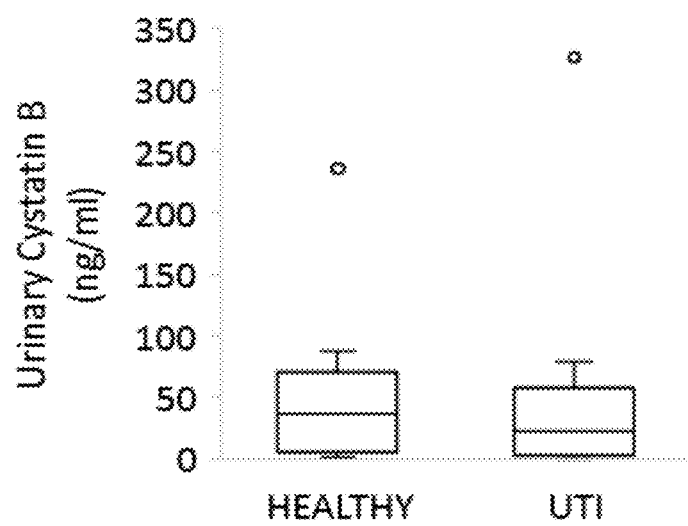
FIG. 8 shows Cystatin B levels in healthy and lower urinary tract infection patients.

Urine samples from 10 dogs each with clinically confirmed Urinary Tract Infection (UTI) and 10 healthy cohorts were run in the Cystatin B assay. UTI was confirmed by positive cultures and clinical examination. Interference from UTI is a major issue for specificity of previously known AKI markers. FIG. 8 demonstrates that Cystatin B levels showed no significant difference between healthy and lower urinary tract infection patients. Therefore, the Cystatin B marker can be used to differentiate between AKI and UTI.

Example 11: Cystatin B in Feline Kidney Disease

Urine samples from four felines diagnosed with renal disease and three healthy controls were obtained from a local veterinary clinic, and were run in the Cystatin B assay. Urinary Cystatin B concentrations in each of the four cats with renal disease exceeded the reference interval of 257 ng/ml. Urinary Cystatin B concentrations in each of the three healthy controls were within the reference interval. See Table 15. Cystatin B is a marker for renal disease in cats.

TABLE 15

| Urinary Cystatin B ng/mL | Serum Creatinine mg/dL | SDMA (ug/dL), or other tests as indicated | Diagnosis |
|---|---|---|---|
| 3062 | 3.0 (Mar. 2, 2016) 2.9 (Apr. 1, 2016) 2.6 (Aug. 27, 2016) | N/D (Mar. 2, 2016) 16 (Apr. 1, 2016) 26 (Aug. 27, 2016) | Renal Disease |
| 1513 | 2.0 (Feb. 13, 2013) 2.4 (Mar. 20, 2014) 3.1 (Oct. 6, 2015) | Urine Protein 30 mg/dL; Urine 250 erythrocytes/uL | Renal Disease |
| 903 | 1.3 (Jul. 17, 2015) 3.6 (Nov. 16, 2015) 2.4 (Nov. 23, 2015) 2.0 (Dec. 10, 2015) 3.8 (Feb. 1, 2016) | N/D | Renal Disease |
| 329 | 2.0 (Feb. 13, 2013) 2.4 (Mar. 20, 2014) 3.1 (Oct. 6, 2015) | Urine Protein 30 mg/dL; Urine 250 erythrocytes/uL | Renal Disease |
| 73 | N/D | N/D | Healthy |
| 50 | N/D | N/D | Healthy |
| 48 | N/D | N/D | Healthy |

N/D = not determined.

Example 12: Anti-Cystatin B Antibodies in Sheep

Two sheep were used to generate sheep polyclonal antibodies against SEQ ID NO:4. The peptide was conjugated to KLH and emulsified in Freund's complete adjuvant. A standard 200 day protocol was used. The antibody response in sheep serum was compared to that of rabbit serum. Similar titers were seen in the sheep even though the sheep were in the early stages of the immunizing protocol. The antibodies raised in sheep can be used for detection of Cys B polypeptides.

TABLE 16

| Dilution | Rabbit | Sheep |
|---|---|---|
| 100 | 2.832 | 2.804 |
| 1000 | 2.753 | 2.986 |
| 10000 | 1.56 | 0.797 |
| 100000 | 0.296 | 0.076 |
| 1000000 | 0.04 | 0.017 |
| 10000000 | 0.008 | 0.001 |

Example 13: Human Urine Cystatin B Detection in CKD Patient

Figure 9:
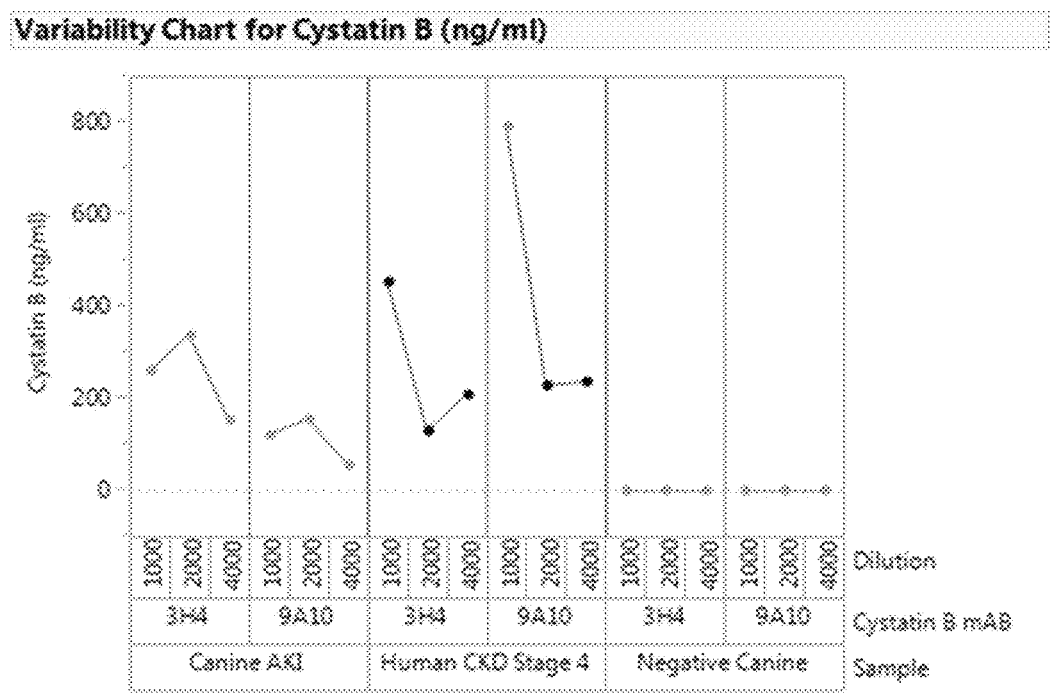
FIG. 9 shows detection of Cys B polypeptides in canine AKI samples, human CKD samples and canine negative control samples.

Urine was collected from a human patient diagnosed with Stage 4 CKD. Urine was serial diluted and run in a Cystatin B urine ELISA. Two anti-Cystatin B monoclonal antibodies (3H4 (see Examples 2 and 3) and 9A10 (see Example 6)) were compared. As shown in FIG. 9, the human urine sample generated higher levels of Cystatin B than the canine AKI sample, and higher levels than the canine negative control. In addition, the different anti-Cystatin B monoclonals showed different responses presumably due to the availability of the epitopes for binding. Therefore, renal disease, including CKD can be diagnosed in humans using antibodies specific for Cystatin B.

What is claimed is:

1. A method for diagnosis and treatment of renal disease in a subject comprising detecting an amount of cystatin B polypeptides, comparing the amount of the cystatin B polypeptides to a control sample or control standard, wherein the cystatin B polypeptides are selected from the group consisting of SEQ ID NOs:2, 3, 5, 6, 7, 11, and 12, diagnosing the subject with renal disease where elevated levels of cystatin B polypeptides compared to the control sample or control standard are present, and treating the subject for acute kidney injury or chronic kidney renal disease, wherein the treating comprises surgery for obstructive nephron/ureteroliths, chemotherapy for renal neoplasia, dietary management, enteric phosphate binders, administration of antiproteinurics, administration of antihypertensives, fluid therapy, management of acidosis, administration of diuretics, dialysis, correction of electrolyte abnormalities, administration of antiemetics, administration of antacids, or administration of recombinant erythropoietin.

2. The method of claim 1, wherein the sample is obtained from a non-human animal.

3. The method of claim 1, wherein the sample is blood, serum, plasma or urine.

4. The method of claim 1, wherein the cystatin B polypeptides are detected by, a competitive immunoassay, a sandwich immunoassay, an enzyme-linked immunosorbent assay (ELISA), a turbidimetric immunoassay, a particle-enhanced turbidimetric immunoassay, a radioimmunoassay (RIA), or a western blot assay.

5. The method of claim 1, wherein the cystatin B polypeptides are detected by an immunoassay.

6. The method of claim 1, wherein the cystatin B polypeptides are SEQ ID NO:2.

7. The method of claim 1, wherein the cystatin B polypeptides are SEQ ID NO:3.

8. The method of claim 1, wherein the cystatin B polypeptides are SEQ ID NO:5.

9. The method of claim 1, wherein the cystatin B polypeptides are SEQ ID NO:6.

10. The method of claim 1, wherein the cystatin B polypeptides are SEQ ID NO:7.

11. The method of claim 1, wherein the cystatin B polypeptides are SEQ ID NO:11.

12. The method of claim 1, wherein the cystatin B polypeptides are SEQ ID NO:12.

* * * * *

```
                         SEQUENCE LISTING

<160> NUMBER OF SEQ ID NOS: 27

<210> SEQ ID NO 1
<211> LENGTH: 77
<212> TYPE: PRT
<213> ORGANISM: Canis familiaris

<400> SEQUENCE: 1

Gln Val Lys Ala Gln Leu Glu Glu Arg Glu Asn Lys Lys Tyr Thr Thr
1               5                   10                  15

Phe Lys Ala Val Thr Phe Arg Ser Gln Val Val Ala Gly Thr Pro Tyr
            20                  25                  30

Phe Ile Lys Val Gln Val Asp Asp Glu Phe Val His Leu Arg Val
            35                  40                  45

Phe Gln Ser Leu Pro His Glu Asn Lys Pro Leu Ala Leu Ser Ser Tyr
    50                  55                  60

Gln Thr Asn Lys Ala Lys His Asp Glu Leu Ala Tyr Phe
65                  70                  75

<210> SEQ ID NO 2
<211> LENGTH: 21
<212> TYPE: PRT
<213> ORGANISM: Canis familiaris

<400> SEQUENCE: 2

Met Met Cys Gly Ala Pro Ser Ala Ser Gln Pro Ala Thr Ala Asp Thr
1               5                   10                  15

Gln Ala Ile Ala Asp
            20

<210> SEQ ID NO 3
```

```
<211> LENGTH: 98
<212> TYPE: PRT
<213> ORGANISM: Canis familiaris
<220> FEATURE:
<221> NAME/KEY: MISC_FEATURE
<222> LOCATION: (52)..(52)
<223> OTHER INFORMATION: The X stands for any amino acid

<400> SEQUENCE: 3
```

Met Met Cys Gly Ala Pro Ser Ala Ser Gln Pro Ala Thr Ala Asp Thr
1               5                   10                  15

Gln Ala Ile Ala Asp Gln Val Lys Ala Gln Leu Glu Glu Arg Glu Asn
            20                  25                  30

Lys Lys Tyr Thr Thr Phe Lys Ala Val Thr Phe Arg Ser Gln Val Val
        35                  40                  45

Ala Gly Thr Xaa Tyr Phe Ile Lys Val Gln Val Asp Asp Asp Glu Phe
    50                  55                  60

Val His Leu Arg Val Phe Gln Ser Leu Pro His Glu Asn Lys Pro Leu
65                  70                  75                  80

Ala Leu Ser Ser Tyr Gln Thr Asn Lys Ala Lys His Asp Glu Leu Ala
                85                  90                  95

Tyr Phe

```
<210> SEQ ID NO 4
<211> LENGTH: 13
<212> TYPE: PRT
<213> ORGANISM: Canis familiaris

<400> SEQUENCE: 4
```

Gln Thr Asn Lys Ala Lys His Asp Glu Leu Ala Tyr Phe
1               5                   10

```
<210> SEQ ID NO 5
<211> LENGTH: 18
<212> TYPE: PRT
<213> ORGANISM: Canis familiaris

<400> SEQUENCE: 5
```

Cys Gly Ala Pro Ser Ala Ser Gln Pro Ala Thr Ala Asp Thr Gln Ala
1               5                   10                  15

Ile Ala

```
<210> SEQ ID NO 6
<211> LENGTH: 8
<212> TYPE: PRT
<213> ORGANISM: Canis familiaris

<400> SEQUENCE: 6
```

Cys Gly Ala Pro Ser Ala Ser Gln
1               5

```
<210> SEQ ID NO 7
<211> LENGTH: 9
<212> TYPE: PRT
<213> ORGANISM: Canis familiaris

<400> SEQUENCE: 7
```

Cys Ala Ile Ala Asp Gln Val Lys Ala
1               5

```
<210> SEQ ID NO 8
<211> LENGTH: 15
```

```
<212> TYPE: PRT
<213> ORGANISM: Canis familiaris

<400> SEQUENCE: 8

Phe Gln Ser Leu Pro His Glu Asn Lys Pro Leu Ala Leu Ser Ser
1               5                   10                  15

<210> SEQ ID NO 9
<211> LENGTH: 18
<212> TYPE: PRT
<213> ORGANISM: Canis familiaris

<400> SEQUENCE: 9

Ser Gln Val Val Ala Gly Thr Pro Tyr Phe Ile Lys Val Gln Val Asp
1               5                   10                  15

Asp Asp

<210> SEQ ID NO 10
<211> LENGTH: 8
<212> TYPE: PRT
<213> ORGANISM: Canis familiaris

<400> SEQUENCE: 10

Lys His Asp Glu Leu Ala Tyr Phe
1               5

<210> SEQ ID NO 11
<211> LENGTH: 29
<212> TYPE: PRT
<213> ORGANISM: Canis familiaris

<400> SEQUENCE: 11

Met Met Cys Gly Ala Pro Ser Ala Ser Gln Pro Ala Thr Ala Asp Thr
1               5                   10                  15

Gln Ala Ile Ala Asp Gln Val Lys Ala Gln Leu Glu Glu
            20                  25

<210> SEQ ID NO 12
<211> LENGTH: 8
<212> TYPE: PRT
<213> ORGANISM: Canis familiaris

<400> SEQUENCE: 12

Ala Ile Ala Asp Gln Val Lys Ala
1               5

<210> SEQ ID NO 13
<211> LENGTH: 18
<212> TYPE: PRT
<213> ORGANISM: Canis familiaris

<400> SEQUENCE: 13

Ser Gln Val Val Ala Gly Thr Asn Tyr Phe Ile Lys Val Gln Val Asp
1               5                   10                  15

Asp Asp

<210> SEQ ID NO 14
<211> LENGTH: 98
<212> TYPE: PRT
<213> ORGANISM: Homo sapiens

<400> SEQUENCE: 14

Met Met Cys Gly Ala Pro Ser Ala Thr Gln Pro Ala Thr Ala Glu Thr
```

```
                1               5                   10                  15
            Gln His Ile Ala Asp Gln Val Arg Ser Gln Leu Glu Glu Lys Glu Asn
                            20                  25                  30

Lys Lys Phe Pro Val Phe Lys Ala Val Ser Phe Lys Ser Gln Val Val
                        35                  40                  45

Ala Gly Thr Asn Tyr Phe Ile Lys Val His Val Gly Asp Glu Asp Phe
                    50                  55                  60

Val His Leu Arg Val Phe Gln Ser Leu Pro His Glu Asn Lys Pro Leu
             65                  70                  75                  80

Thr Leu Ser Asn Tyr Gln Thr Asn Lys Ala Lys His Asp Glu Leu Thr
                                85                  90                  95

Tyr Phe
```

<210> SEQ ID NO 15
<211> LENGTH: 13
<212> TYPE: PRT
<213> ORGANISM: Homo sapiens

<400> SEQUENCE: 15

```
Gln Thr Asn Lys Ala Lys His Asp Glu Leu Thr Tyr Phe
1               5                   10
```

<210> SEQ ID NO 16
<211> LENGTH: 12
<212> TYPE: PRT
<213> ORGANISM: Canis familiaris

<400> SEQUENCE: 16

```
Gln Thr Asn Lys Ala Lys His Asp Glu Leu Ala Tyr
1               5                   10
```

<210> SEQ ID NO 17
<211> LENGTH: 11
<212> TYPE: PRT
<213> ORGANISM: Canis familiaris

<400> SEQUENCE: 17

```
Gln Thr Asn Lys Ala Lys His Asp Glu Leu Ala
1               5                   10
```

<210> SEQ ID NO 18
<211> LENGTH: 10
<212> TYPE: PRT
<213> ORGANISM: Canis familiaris

<400> SEQUENCE: 18

```
Gln Thr Asn Lys Ala Lys His Asp Glu Leu
1               5                   10
```

<210> SEQ ID NO 19
<211> LENGTH: 9
<212> TYPE: PRT
<213> ORGANISM: Canis familiaris

<400> SEQUENCE: 19

```
Gln Thr Asn Lys Ala Lys His Asp Glu
1               5
```

<210> SEQ ID NO 20
<211> LENGTH: 4
<212> TYPE: PRT
<213> ORGANISM: Canis familiaris

```
<400> SEQUENCE: 20

Leu Ala Tyr Phe
1

<210> SEQ ID NO 21
<211> LENGTH: 5
<212> TYPE: PRT
<213> ORGANISM: Canis familiaris

<400> SEQUENCE: 21

Glu Leu Ala Tyr Phe
1               5

<210> SEQ ID NO 22
<211> LENGTH: 6
<212> TYPE: PRT
<213> ORGANISM: Canis familiaris

<400> SEQUENCE: 22

Asp Glu Leu Ala Tyr Phe
1               5

<210> SEQ ID NO 23
<211> LENGTH: 7
<212> TYPE: PRT
<213> ORGANISM: Canis familiaris

<400> SEQUENCE: 23

His Asp Glu Leu Ala Tyr Phe
1               5

<210> SEQ ID NO 24
<211> LENGTH: 9
<212> TYPE: PRT
<213> ORGANISM: Canis familiaris

<400> SEQUENCE: 24

Ala Lys His Asp Glu Leu Ala Tyr Phe
1               5

<210> SEQ ID NO 25
<211> LENGTH: 10
<212> TYPE: PRT
<213> ORGANISM: Canis familiaris

<400> SEQUENCE: 25

Lys Ala Lys His Asp Glu Leu Ala Tyr Phe
1               5                   10

<210> SEQ ID NO 26
<211> LENGTH: 11
<212> TYPE: PRT
<213> ORGANISM: Canis familiaris

<400> SEQUENCE: 26

Asn Lys Ala Lys His Asp Glu Leu Ala Tyr Phe
1               5                   10

<210> SEQ ID NO 27
<211> LENGTH: 12
<212> TYPE: PRT
<213> ORGANISM: Canis familiaris

<400> SEQUENCE: 27
```

```
Thr Asn Lys Ala Lys His Asp Glu Leu Ala Tyr Phe
1               5                   10
```